United States Patent [19]

Hershberger et al.

[11] Patent Number: 4,732,859

[45] Date of Patent: * Mar. 22, 1988

[54] METHOD FOR CONFERRING BACTERIOPHAGE RESISTANCE TO BACTERIA

[75] Inventors: Charles L. Hershberger, New Palestine; Paul R. Rosteck, Jr., Beech Grove, both of Ind.

[73] Assignee: Eli Lilly and Company, Indianapolis, Ind.

[*] Notice: The portion of the term of this patent subsequent to Jul. 23, 2002 has been disclaimed.

[21] Appl. No.: 647,338

[22] Filed: Sep. 5, 1984

Related U.S. Application Data

[63] Continuation of Ser. No. 414,290, Sep. 3, 1982, Pat. No. 4,530,904.

[51] Int. Cl.[4] ........................ C12N 9/14; C12N 1/20; C12N 1/00; C12N 15/00; C12N 9/10; C12P 21/00
[52] U.S. Cl. ..................................... 435/320; 435/68; 435/172.1; 435/172.3; 435/193; 435/195; 435/253; 935/29; 935/72; 935/73; 935/74; 935/75; 935/79
[58] Field of Search ............... 435/68, 70, 91, 172.3, 435/253, 317, 317.1, 193, 195, 172.1; 935/29, 72–75, 79

[56] References Cited

U.S. PATENT DOCUMENTS 4,530,904  7/1985  Hershberger et al. ........... 435/172.3

OTHER PUBLICATIONS

Chater et al, "Restriction of a Bacteriophage in Streptomyces Albus P (CMI 52766), by Endonuclease SalPI", J. Gen. Microbiol., 109: 181 (1978).
Chater et al, "A New, Wide Host-Range, Temperature Bacteriophage (R4) of Streptomyces and Its Interaction with Some Restriction-Modification Systems", J. Gen. Microbiol., 115: 431 (1979).
Helling et al, "The Molecular Cloning of Genes-General Procedures", in *Genetic Engineering*, Chakrabarty (ed.), CRC Press, Inc., 1978, pp. 1–29.
Roberts et al, "A General Method for Maximizing the Expression of a Cloned Gene", Proc. Natl. Acad. Sci., USA, 76: 760 (1979).
Mann, M. B. et al., 1978, Gene, 3:97.
Walder, R. Y. et al., 1981, Proc. Natl. Acad. Sci., USA, 78(3):1503.
Newman, A. K. et al., 1981, J. Biol. Chem., 256(5):2131.
Greene, P. J. et al., 1981, J. Biol. Chem., 256(5):2143.
Wesley, Peter, 1982, Genetic Engineering News, May/-Jun. 1982, p. 16.

*Primary Examiner*—James Martinell
*Attorney, Agent, or Firm*—Gerald V. Dahling; Leroy Whitaker

[57] ABSTRACT

A novel method for protecting a bacterium from a naturally occurring bacteriophage and the cloning vectors and transformants for carrying out the aforementioned method are disclosed.

15 Claims, 12 Drawing Figures

Restriction Site and Functional Map of Plasmid pIA7 Δ 4 Δ 1
(5270 bp) Arrows Indicate Direction of Transcription

Restriction Site and Functional Map of Plasmid pIB7Δ4Δ1
(5295 bp) Arrows Indicate Direction of Transcription

Restriction Site Map of Plasmids pPR28 and pPR1228

Restriction Site and Functional Map of Plasmid pHI7 Δ4 Δ1
(5560 bp) Arrows Indicate Direction of Transcription Restriction Site Map of
Plasmid pPR29**

Figure 7
Thymosin Alpha I Gene

```
        1   2   3   4   5   6   7   8   9  10  11  12  13  14  15  16  17  18  19  20  21  22  23  24  25  26  27  28
       Met Ser Asp Ala Ala Val Asp Thr Ser Ser Glu Ile Thr Thr Lys Asp Leu Lys Glu Lys Lys Glu Val Val Glu Glu Ala Glu Asn                stop stop
EcoRI
───►
|◄──── T₁ ────►|◄──── T₂ ────►|◄──── T₃ ────►|◄──── T₄ ────►|                                                                               |◄── T₁₂ ──►|
AATTCATGTCTGATGCTGCTGTTGATACTTCTTCTGAGATTACTACTAAA GATCTTAAGGAGAAGAAGGAAGTTGTCGAAGAGGCTGAGAACTAATAG
GTACAGACTACGACGACAACTATGAAGAAGACTCTAATGATGATTT CTAG AATTCCTCTTCTTCCTTCAACAGCTTCTCCGACTCTTGATTATCCTAG
        |◄──── T₅ ────►|◄──── T₆ ────►|◄──── T₇ ────►|◄──── T₈ ────►|◄──── T₁₃ ────►|◄──── T₁₄ ────►|◄──── T₁₅ ────►|◄── T₁₆ ──►|
                                                              BglII                                                                        BamHI
```

Synthesis Procedure for Fragment T_15

Construction Route for Plasmid pThα1

Proinsulin Synthetic Gene

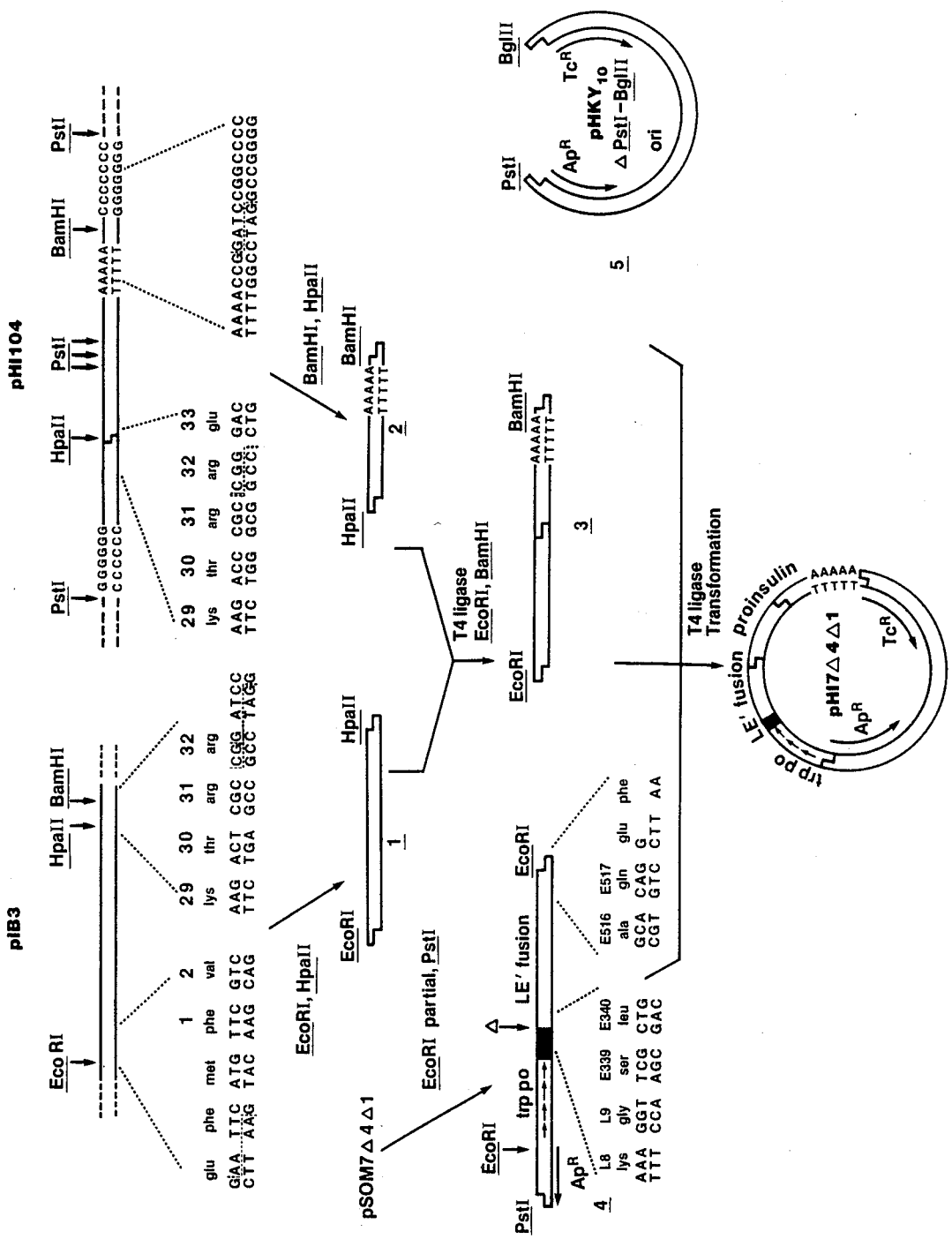

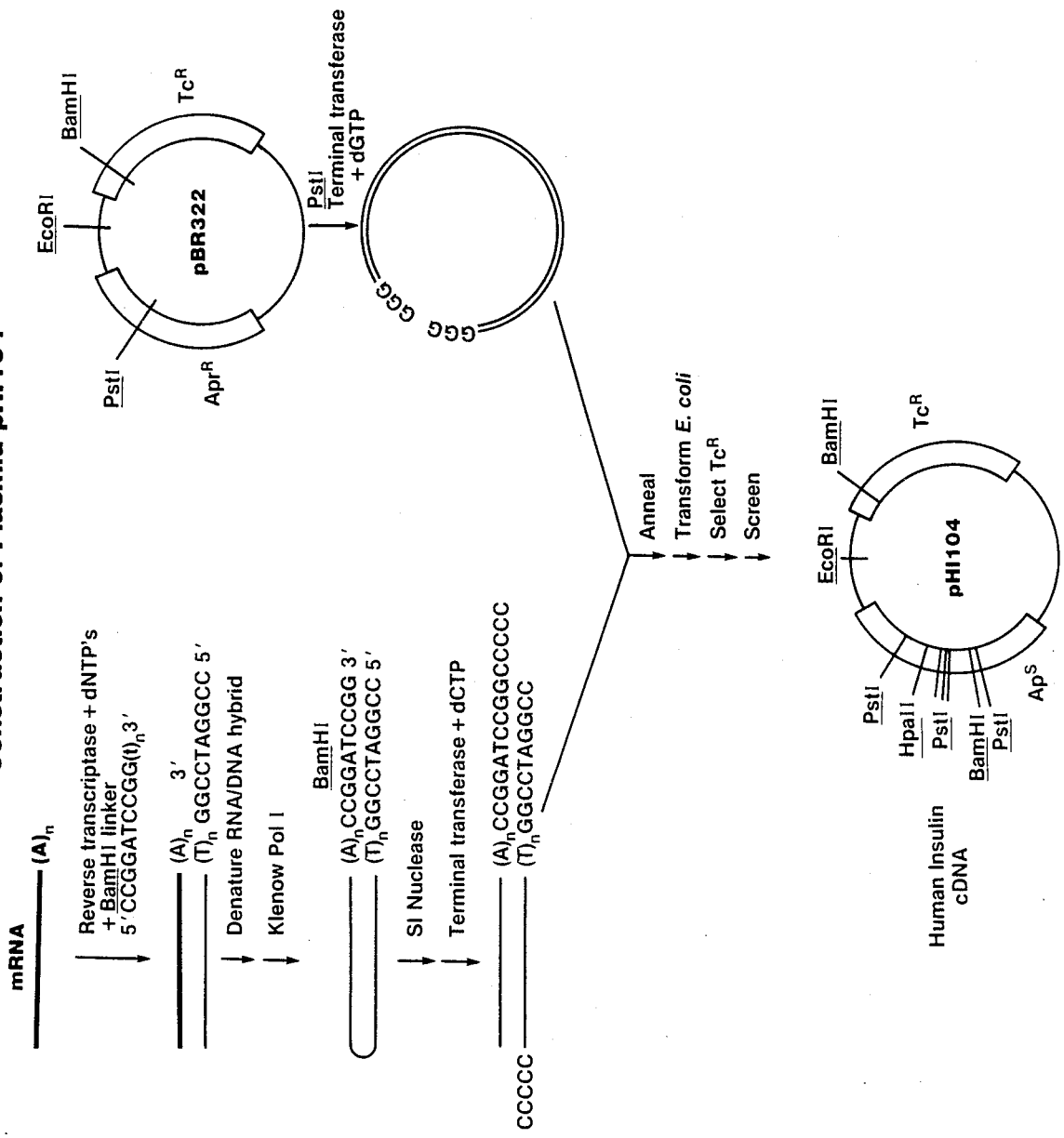

4,732,859

METHOD FOR CONFERRING BACTERIOPHAGE RESISTANCE TO BACTERIA

This application is a continuation of application Ser. No. 414,290 filed Sept. 3, 1982, now U.S. Pat. No. 4,530,904, issued Sept. 2, 1987.

SUMMARY OF THE INVENTION

The present invention comprises a novel method of protecting bacteria from naturally occurring bacteriophage. The invention further comprises the cloning vectors and transformants employed in the aforementioned method.

The present invention is particularly important because it solves the problem of massive phage infection of recombinant DNA-containing bacterial cultures. This is advantageous because once recombinant DNA coding for a desired product is transformed into a host cell, it is desirable, if not essential, that the host cell be protected against bacteriophage infection. Such protection is crucial since transformant cultures are notoriously susceptible to bacteriophage which, upon infection, lyse whole populations. Since the genetic expression of a product is dependent on the host cells remaining alive long enough for the desired biosynthesis to occur, the productive capacity of infected cultures is reduced.

Phage infection of microorganisms is a known phenomenon. Usually the virus, or bacteriophage in the case of bacterial infection, makes contact, undergoes adsorption, and reacts with the host's cell membrane. The adsorption allows the phage-chromosome or genetic material to enter the host cell and begin a process whereby the host's cellular machinery is subjugated and used exclusively for the production of new phage. The host cell becomes filled with mature phage and then undergoes lysis, usually within about 30 minutes from the time of the initial infection. The new phage are infectious and the cycle repeats until all the available host cells are destroyed.

Heretofore, the exploitation of recombinant DNA technology by large scale fermentation of *E. coli* has been hindered by the aforementioned problem of phage infection. In fact, infection involving a diverse flora of bacteriophage is a major factor that prevents and interferes with the biosynthesis of desired products. This problem becomes most acute during large scale fermentation and can result in a costly and precipitous loss of *E. coli* transformant populations. These losses can involve bacterial populations of entire fermentation tanks and consequently threatens the industrial application and exploitation of recombinant DNA technology.

The present invention solves the bacteriophage problem by providing an inexpensive and effective means for protecting bacterial transformants from naturally occurring bacteriophage. This is done by providing host cells with a restriction system that digests HhaII site-containing foreign DNA. The HhaII site is found in most naturally occurring viruses so therefore the present invention is effective against a wide array of troublesome bacteriophage. Thus, as phage DNA enters a host cell with the present invention in place, the HhaII restriction endonuclease digests the DNA at HhaII sites and renders the phage non-functional and harmless. In this way the bacterial host cells are protected from naturally occurring bacteriophage therefore insuring the productivity of the culture. This is not only advantageous but represents a significant advance in the technical art.

Very few, if any, other methods have been described for solving the bacteriophage problem associated with large scale fermentation of *E. coli* and other bacteria. In fact, bacteriophage infection has been known to occur even under the most extraordinarily aseptic conditions and, once present, bacteriophage are notoriously difficult to eliminate. Although such elimination is possible, it is very inconvenient and expensive in terms of time and lost production. Furthermore, the very occurrence of bacteriophage threatens fermentation in areas proximate to the infection. The present invention provides an effective and commercially feasible method for solving the bacteriophage problem and therefore is important to the industrial and commercial application of recombinant DNA technology.

For purposes of the present invention disclosed herein, the following terms are as defined below.

Recombinant DNA cloning vector—any agent capable of replication, including but not limited to plasmids, bacteriophages, and viruses, comprising a DNA molecule to which one or more additional DNA segments can or have been added.

Transformation—the introduction of DNA into a recipient host cell that changes the genotype and results in a change in the recipient cell.

Functional Polypeptide—a recoverable bioactive entirely heterologous polypeptide or precursor, a recoverable bioactive polypeptide comprising a heterologous polypeptide and a portion or whole of a homologous polypeptide, a recoverable bioinactive fusion polypeptide comprising a heterologous polypeptide and a bio-inactivating homologous polypeptide which can be specifically cleaved, or a polypeptide with an enzymatic function.

Fused Gene Product—a recoverable heterologous polypeptide which is fused with a portion or whole of a homologous polypeptide.

Marker—a gene or combination of genes of known function and location on a chromosome or recombinant DNA cloning vector.

Transformant—a recipient host cell that has undergone transformation.

Sensitive Bacterium—a bacterium that becomes infected when grown in the presence of a phage.

Restriction Fragment—any linear portion or whole of a plasmid, other vector, or chromosomal DNA which is generated by the action of one or more restriction enzymes.

Insertional Isomer—one of two or more possible recombinant DNA molecules formed when a DNA fragment is inserted at one of two or more compatible sites on the recipient DNA.

R-M System—a restriction and modification system.
Amp$^R$—the ampicillin resistant phenotype.
Amp$^s$—the ampicillin sensitive phenotype.
Tet$^R$—the tetracycline resistant phenotype.
Tet$^S$—the tetracycline sensitive phenotype.

BRIEF DESCRIPTION OF THE DRAWINGS

FIG. 7 depicts the DNA sequence and encoded amino acid residue sequence of the thymosin alpha 1 gene and the synthetic fragments used to construct the thymosin alpha 1 gene.

FIG. 11 depicts the construction route for plasmid pHI7Δ4Δ1.

FIG. 12 depicts the construction route for plasmid pHI104.

DETAILED DESCRIPTION OF THE INVENTION

The present invention is a method for protecting a bacterium from a naturally occurring bacteriophage comprising transforming said bacterium with a recombinant DNA cloning vector, said vector comprising (1) a DNA segment that confers a restriction cognate modification activity to said bacterium,
(2) a replicon that is functional in said bacterium, and
(3) a gene that expresses a functional polypeptide in said bacterium, subject to the limitation that (1) said naturally occurring bacteriophage contains double stranded DNA with a restriction site of the same specificity as the restriction activity conferred to said bacterium, and (2) that said modification activity is expressed in said bacterium prior to said restriction activity.

The invention further comprises the cloning vectors and transformants employed in the aforementioned method and is important for insuring the successful large scale fermentation of microorganisms which produce products coded for by recombinant DNA. Without a restriction and modification system, many cultures become infected by bacteriophage thereby reducing bioproduction of a desired product.

The HhaII restriction-modification system of *Haemophilus haemolyticus* is employed to exemplify the present invention. The genes comprising the HhaII R-M system are closely linked and result in the synthesis of HhaII restriction endonuclease and also a cognate methylase enzyme. The HhaII restriction enzyme recognizes and cleaves double stranded DNA with the sequence $$\frac{GANTC}{CTNAG}.$$

hereinafter the HhaII site, while the cognate modification system methylates certain nucleotides of the aforementioned sequence. Those skilled in the art will recognize that the methylase enzyme modification system must be expressed before the HhaII restriction enzyme is bio-synthesized. Cells containing the HhaII R-M system are thus protected against HhaII digestion but will digest foreign non-modified double stranded DNA that contains the HhaII site. Therefore, the HhaII R-M system is ideal for purposes of exemplifying the present invention.

Figure 1:
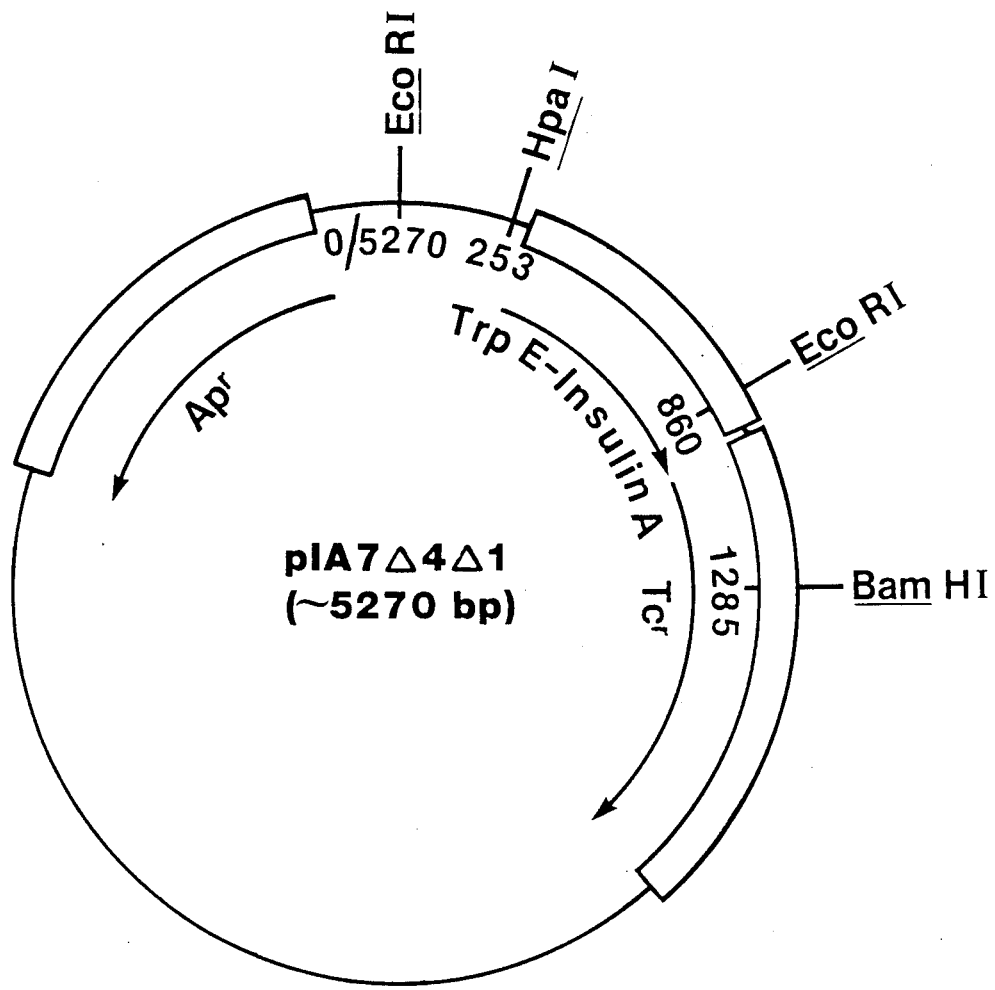
FIG. 1 is a restriction site and function map of plasmid pIA7Δ4Δ1.

More particularly, the present invention is exemplified by cloning the ~2.7 kb PstI restriction fragment of plasmid pDI10 into the insulin A chain plasmid pIA7Δ4Δ1. Plasmid pIA7Δ4Δ1 contains the *E. coli* tryptophan promoter, antibiotic resistance markers, and a gene which expresses a fused gene product comprising a portion of the *E. coli* K12 trp E protein fused with the A polypeptide chain of human insulin. A restriction site and functional map of plasmid pIA7Δ4Δ1 is presented in FIG. 1 of the accompanying drawings.

The ~2.7 kb PstI fragment of plasmid pDI10 contains genes for restriction and modification with the specificity of HhaII. Plasmid pDI10 can be isolated from *E. coli* K12 294/pDI10, a strain deposited and made part of the permanent stock culture collection, Northern Regional Research Laboratory, Peoria, Ill. It is available to the public as a preferred source and stock reservoir of plasmid pDI10 under the accession number B-15097.

With regard to conventions, the symbol "Δ" connotes a deletion. Thus, for example, reference to a plasmid followed by, "ΔEcoRI-XbaI" describes the plasmid from which the nucleotide sequence between EcoRI and XbaI restriction enzyme sites has been removed by digestion with those enzymes. For convenience, certain deletions are denoted by number. Thus, beginning from the first base pair ("bp") of the EcoRI recognition site which precedes the gene for tetracycline resistance in the parental plasmid pBR322, "Δ1" connotes deletion of bp 1–30 (ie, ΔEcoRI-HindIII) and consequent disenabling of the tetracycline promoter/operator system; "Δ2" connotes deletion of bp 1–375 (ie, ΔEcoRI-BamHI) and consequent removal of both the tetracycline promoter/operator and a portion of the structural gene which encodes tetracycline resistance; and "Δ4" connotes deletion of bp ~900–~1500 from the trp operon fragment eliminating the structural gene for the trp D polypeptide.

Figure 2:
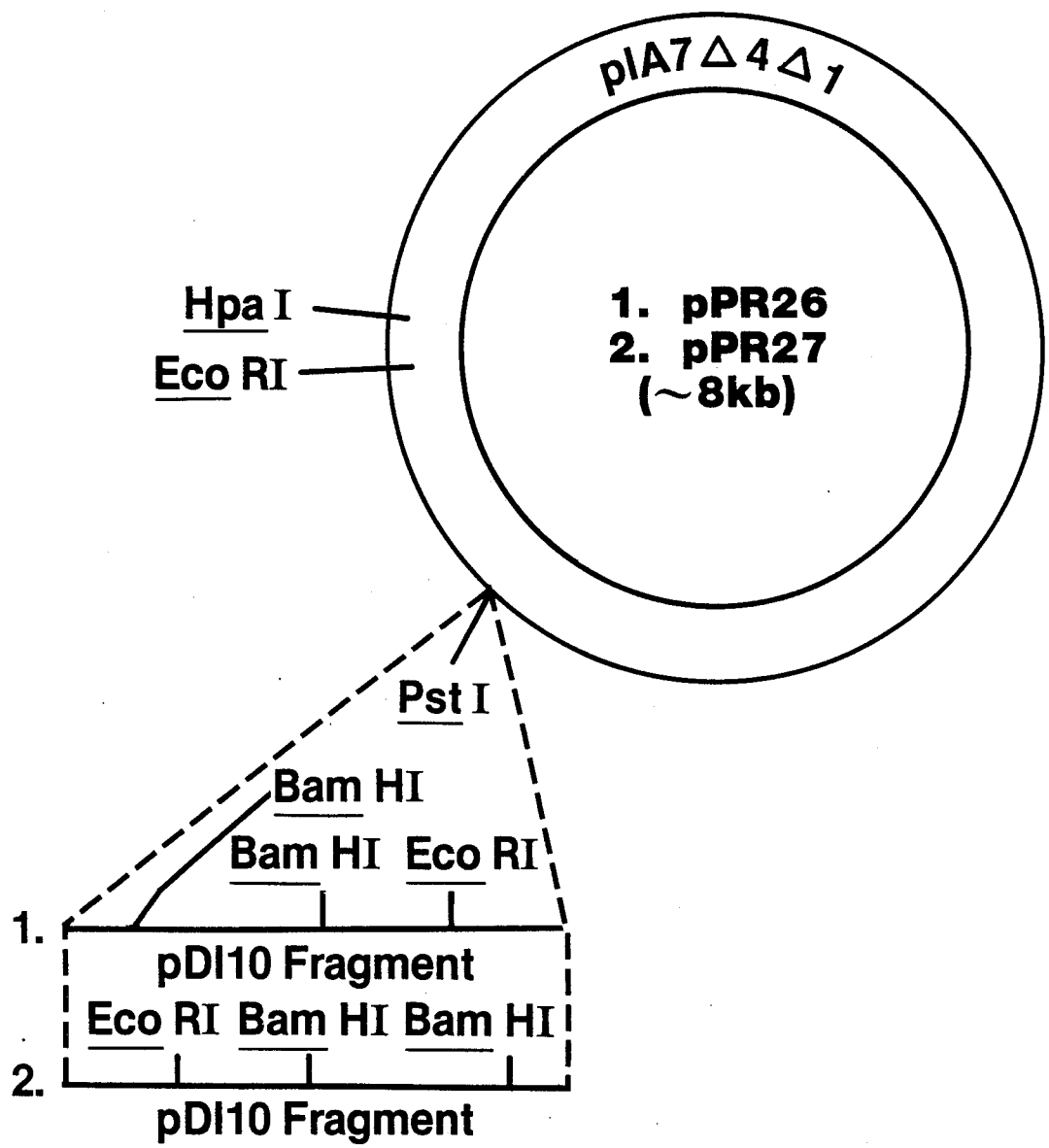
FIG. 2 is a restriction site map of plasmids pPR26 and pPR27.

The cloning of the ~2.7 kb PstI HhaII R-M gene-containing restriction fragment of plasmid pDI10 into plasmid pIA7Δ4Δ1 results in the novel plasmids pPR26 and pPR27. Both plasmids protect bacteria such as, for example, various *E. coli* strains, against infection from naturally occurring bacteriophage. A restriction site map of each of plasmids pPR26 and pPR27 is presented in FIG. 2 of the accompanying drawings.

The novel plasmids pPR28 and pPR1228 can also be constructed to further exemplify the present invention. Plasmids pPR28 and pPR1228 result from the insertion of the ~2.7 kb PstI HhaII R-M gene-containing restriction fragment of plasmid pDI10 into plasmid pIB7Δ4Δ1. Plasmid pIB7Δ4Δ1 contains the *E. coli* tryptophan promoter, antibiotic resistance markers, and a gene which expresses a fused gene product comprising a portion of the *E coli* K12 trp E protein fused with the B polypeptide chain of human insulin. Plasmids pPR28 and pPR1228 also protect bacteria such as, for example, various *E. coli* strains, from naturally occurring bacteriophage. A restriction site and functional map of plasmid pIB7Δ4Δ1 and each of plasmids pPR28 and pPR1228 are presented respectively in FIGS. 3 and 4 of the accompanying drawings.

Ligation of the ~6.2 kb AvaI-BglII HhaII R-M gene-containing restriction fragment of plasmid pPR27 and the ~2.3 kb AvaI-BglII restriction fragment of plasmid pHI7Δ1Δ4 results in the novel plasmid pPR29. Plasmid pHI7Δ4Δ1 contains the *E. coli* tryptophan promoter, antibiotic resistance markers, and a gene which expresses a fused gene product comprising a portion of the *E coli* K12 trp E protein fused with the human proinsulin polypeptide. Plasmid pPR29 confers restriction and modification activity and thus protects bacteria such as, for example, various *E. coli* strains, against infection from naturally occurring bacteriophage. A restriction site and functional map of each of plasmids pHI7Δ4Δ1 and pPR29 is presented respectively in FIGS. 5 and 6 of the accompanying drawings.

The present invention is particularly versatile and can be applied to the production of any substance where synthesis is determined either by DNA comprising a recombinant DNA cloning vector or by an endogenous metabolic pathway. A preferred recombinant DNA cloning vector, for illustrative purposes, is the plasmid although bacteriophage, cosmid, and other vectors can also be used and will be apparent to those skilled in the art. The invention can also employ genes for any restriction and modification system provided that the genes are coordinately expressed such that the modification function is expressed in advance of the restriction function. Since the usefulness of the present invention is independent of markers or other genes cloned into the cloning vector, the invention can be used with recombinant or other strains that carry one or more genes of commercial or research value.

A preferred embodiment of the present invention employs plasmid borne restriction and modification genes with the specificity of HhaII for protecting bacteria from naturally occurring bacteriophage. In addition, genes for R-M systems with other specificities can also be used. These include, for example, genes for the PstI R-M system (Walder et al., 1981, Proc. Natl. Acad. Sci. USA 78(3) 1503), EcoR1 R-M system (Jack et al., 1980, Fed. Proc. Fed. Am. Soc. Exp. Biol. 39:1875), and TaqI R-M system (Lan-Hsiaing, et al., 1982, Federation Proc. 41:5427). Genes for the TaqI R-M system can be conventionally cloned from *Thermus aquaticus* YT-1 (Brock and Freeze, 1969, J. of Bacteriology, 98(1):289, type strain ATCC No. 25104) in substantial accordance with the methodology of Mann et al., 1978, Gene 3:97. As with the HhaII R-M system, the genes for modification must be expressed before the genes for restriction. Use of the aforementioned genes separately or in combination with genes for the HhaII or other R-M systems protects bacteria from naturally occurring bacteriophage and thus is within the scope of the present invention.

The present method for protecting bacteria from naturally occurring bacteriophage can be imposed on hose cells containing vectors with genes that express a variety of useful products. Although the R-M genes may be borne on a separate vector, the cloning of the R-M genes into a plasmid simultaneously containing a gene which expresses a useful product is preferred. A gene which expresses a useful polypeptide product may be naturally occurring, non-naturally occurring, or in part naturally occurring and in part synthetic or non-naturally occurring. More particularly, the genes for a R-M system can be cloned into plasmids containing a gene coding for and expressing human pre-proinsulin, human proinsulin, human insulin A-chain, human insulin B-chain, human growth hormone, non-human growth hormone, bovine growth hormone, non-human insulin, human interferon, non-human interferon, viral antigen, urokinase, any enzyme conferring antibiotic resistance, any peptide hormone, any peptide enzyme, or for virtually any other peptide with research or commercial value.

In the specific embodiments of the invention described herein, plasmid replication and expression of polypeptide product are determined respectively by the polA gene-requiring replicon from pMB1 (disclosed in Bolivar, 1979, Life Sci. 25:807–818) and by the trp promoter. Other replicons and promoters can also be used so long as they are functional in the particular bacterial transformant being protected. It is understood that those skilled in the art know or readily can determine which replicons and promoters are preferred for use in a particular bacterium. Examples of other replicons include, but are not limited to, replicons from ColE1, NR1, RK2, RK6, pSC101, RP1, RP4, F, and the like, including bacteriophage that replicate in *E. coli* K12. Examples of other promoters include, but are not limited to, the bacteriophage $\lambda P_L$ promoter, lipoprotein promoter, lac promoter, ribosomal protein or RNA promoters, and virtually any other promoter. Those skilled in the art will understand that a variety of replicons and promoters can be constructed and used in the R-M system gene-containing vectors of the present invention.

The wealth of genetic and biochemical information about *E. coli* makes it a convenient and preferred bacterial host for purposes of the present invention. Moreover, since *E. coli* K12 is the host cell of choice for the bioproduction of compounds by recombinant DNA technology, the applicability of the present invention to strains of that organism is distinctly advantageous. As discussed herein above, large scale fermentation of *E. coli* has been fraught with difficulty associated with phage infection. The present invention substantially solves this problem and thus allows for the commercial production of biosynthetic products.

The present method is not limited, however, to any one genus, species or strain but can be used with any microorganism in which genes for a R-M system can be cloned. For example, the invention is applicable to prokaryotes generally and, more particularly, to bacteria including, but not limited to, *E. coli*, *E. coli* K12, *E. coli* K12 294 (disclosed in Goeddel et al., 1979, Proc. Nat. Acad. Sci. USA 76:106), *E. coli* K12 RV308 (disclosed in Mauer et al., 1980, J. Mol. Biol. 139:147), *E. coli* K12 C600 (disclosed in Bachman, 1972, Bacteriol. Rev. 36:526), *E. coli* K12 C600R$_k$-M$_k$-(disclosed in Chang and Cohen, 1974, Proc. Nat. Acad. Sci. USA 71:1030), *E. coli* K12 HB101 (Boliver et al., 1977, Gene 2:75), E. coli K12 BE827 ATCC 31911), *Bacillus, Bacillus subtilis, Bacillus thuringiensis, Bacillus megaterium, Staphylococcus, Streptococcus, Actinomycetis, Streptomyces, Agrobacterium, Serratia, Pseudomonas*, and any other bacterium which is susceptible to bacteriophage infection and in which genes for a R-M system can be cloned.

Preferred cloning vectors of the present invention include plasmids pPR27, pPR28, and pPR29 and preferred transformants include *E. coli* K12 RV308/pPR27, *E. coli* K12 RV308/pPR28, and *E. coli* K12 RV308/pPR29. These and all the other embodiments of the present invention share the common feature of protecting bacteria against infection from naturally occurring bacteriophage. Therefore, the present invention allows for large scale fermentation of recombinant DNA-containing microorganisms without a substantial risk of phage infection, lysis, and the concurrent loss of biosynthetic capacity.

The following examples illustrate the present invention in greater detail. Both an explanation of and the actual procedures for constructing the invention are described where appropriate.

EXAMPLE 1

Isolation and Preparation of Plasmid pDI10

About 1 μg. or pladmid pDI10 DNS (isolated from *E. coli* K12 294/pDI10, NRRL B-15097, in substantial accordance with the isolation procedure of Bazaral and Helinski, 1968, J. Mol. Biol. 36:185) was dissolved in TE buffer [1 mM EDTA (ethylene diamine tetraacetate) and 10 mM Tris-HCl, pH 7.8] to a concentration of approximately 20 μg./ml. Since *E. coli* K12 294 is a $R_k^- M_k^+$ host, plasmid DNA can be isolated with methylation according to the EcoK-specifity. About 5 μl. of the solution (containing about 0.1 μg of DNA) was diluted to 50 μl. in SSC/10 (SSC=Standard Saline Citrate buffer and SSC/10 contains 15 mM NaCl and 1:5 mM Na$_3$-Citrate, pH 7). About 25 μl. of the SSC/10-DNA solution was then mixed with 50 μl. of a competent suspension of *E. coli* K12 C600$R_k^- M_k^-$.

A competent suspension of *E. coli* K12 C600-$R_k^- M_k^-$ (Chang and Cohen, 1974, Proc. Nat. Acad. Sci USA 71:1030), was prepared by conventional procedures well known in the art. Accordingly, fresh overnight cultures in L-broth (Miller, 1972, *Experiments in Molecular Genetics*, Cold Spring Harbor Laboratory, Cold Spring Harbor, N.Y.) were subcultured 1/10 in fresh L-broth and grown at 37° C. for 1 hour. A total of 660 Klett Units of cells were harvested, washed with 2.5 ml. of 100 mM NaCl, suspended in 2.5 ml. of 150 mM CaCl$_2$ and incubated at room temperature for 20 minutes. The cells were harvested, resuspended in 0.5 ml. of a solution comprising 150 mM CaCl$_2$ and 10% glycerol, chilled on ice for 3-5 minutes, and then frozen. The suspensions of frozen-competent cells were stored in liquid nitrogen until use. Preservation and storage did not adversely affect the viability or frequency of transformation by covalently closed circular plasmid DNA. The cell-suspension was thawed in an ice bath and mixed with ½ volume of DNA for transformation. The transformation mixture was chilled on ice for 20 minutes, heat-shocked at 42° C. for 1 minute, chilled on ice for 10 minutes, then diluted with 5.7 volumes of L-broth and lastly incubated at 37° C. for 90 minutes.

Transformants were isolated by growth on L-agar containing tetracycline at 12.5 μg./ml. Isolates were tested to verify tetracycline resistance and ampicillin sensitivity and constituted the desired *E. coli* K12 C600$R_k^- M_k^-$/pDI10 transformants. Appropriate colonies were employed to isolate covalently closed circular DNA as described in Bazaral and Helinski, 1968. The structure of the plasmid was verified by mapping restriction sites.

EXAMPLE 2

Construction of Plasmid pIA7Δ4Δ1

A. Construction of Plasmid pBRHtrp

Plasmid pGM1 carries the *E. coli* tryptophan operon containing the deletion ΔLE1413 (Miozzari, et al., 1978, *J. Bacteriology*, 1457-1466) and hence expresses a fusion protein comprising the first 6 amino acids of the trp leader and approximately the last third of the trp E polypeptide (hereinafter referred to in conjunction as LE'), as well as the trp D polypeptide in its entirety, all under the control of the trp promoter-operator system. *E. coli* K12 W3110tna2trpΔ102/pGM1 has been deposited with the American Type Culture Collection (ATCC No. 31622) and pGM1 may be conventionally removed from the strain for use in the procedures described below.

About 20 μg. of the plasmid were digested with the restriction enzyme PvuII which cleaves the plasmid at five sites. The gene fragments were next combined with EcoRI linkers (consisting of a self complementary oligonucleotide of the sequence: pCATGAATTCATG) providing an EcoRI cleavage site for later cloning into a plasmid containing an EcoRI site. The 20 μg of DNA fragments obtained from pGM1 were treated with 10 units T$_4$ DNA ligase in the presence of 200 pico moles of the 5'-phosphorylated synthetic oligonucleotide pCATGAATTCATG and in 20 μl. T$_4$ DNA ligase buffer (20 mM tris, pH 7.6, 0.5 mM ATP, 10 mM MgCl$_2$, 5 mM dithiothreitol) at 4° C. overnight. The solution was then heated 10 minutes at 70° C. to halt ligation. The linkers were cleaved by EcoRI digestion and the fragments, now with EcoRI ends, were separated using 5 percent polyacrylamide gel electrophoresis (herein after "PAGE"). The three largest fragments were isolated from the gel by first staining with ethidium bromide and then locating the fragments with ultraviolet light and cutting from the gel the portions of interest. Each gel fragment, with 300 microliters 0.1xTBE, was placed in a dialysis bag and subjected to electrophoresis at 100 v for one hour in 0.1xTBE buffer (TBE buffer contains: 10.8 gm tris base, 5.5 gm. boric acid, 0.09 gm. Na$_2$EDTA in 1 liter H$_2$O). The aqueous solution was collected from the dialysis bag, phenol extracted, chloroform extracted, and made 0.2 M with respect to sodium chloride. The DNA was then recovered in water after ethanol precipitation. The trp promoter/operator-containing gene with EcoRI sticky ends was identified in the procedure next described, which entails the insertion of fragments into a tetracycline sensitive plasmid which, upon promoter/operator insertion, becomes tetracycline resistant. All DNA fragment isolations hereinafter described are performed using PAGE followed by the electroelution method described above.

B. Construction of Plasmid pBRH trp Expressing Tetracycline Resistance Under the Control of the Trp Promoter/Operator and Identification and Amplification of the Trp Promoter/Operator-Containing DNA Fragment Isolated in 'A' above Plasmid pBRH1, (Rodriguez, et al., 1979, Nucleic Acids Research 6, 3267-3287) expresses ampicillin resistance and contains the gene for tetracycline resistance but, there being no associated promoter, does not express that resistance. The plasmid is accordingly tetracycline sensitive. By introducing a promoter/operator system in the EcoRI site, the plasmid can be made tetracycline resistant.

Plasmid pBRH1 was digested with EcoRI. The enzyme was removed by phenol extraction followed by chloroform extraction and then the DNA was recovered in water after ethanol precipitation. The resulting DNA molecule was, in separate reaction mixtures, combined with each of the three DNA fragments obtained in Example 2A above and ligated with T$_4$ DNA ligase as previously described. The DNA present in the reaction mixture was used to transform competent *E. coli* K12 294 by standard techniques (Hershfield et al., 1974, Proc. Nat. Acad. Sci. USA 71:3455-3459) and the bacteria were then plated on LB plates (Miller, 1972) containing 20 μg./ml. ampicillin and 5 μg./ml. tetracycline.

Several tetracycline-resistant colonies were selected and the plasmid DNA was isolated and designated pBRHtrp. The presence of the desired fragment was confirmed by restriction enzyme analysis. Plasmid pBRH trp expresses β-lactamase, imparting ampicillin resistance, and contains a DNA fragment which includes the trp promoter/operator. The DNA fragment also codes for a first protein, (designated LE'), comprising a fusion of the first six amino acids of the trp leader and approximately the last third of the trp E polypeptide, a second protein (designated D'), corresponding to approximately the first half of the trp D polypeptide, and a third protein, coded for by the tetracycline resistance gene.

C. Construction of Plasmid pSOM7Δ2

Plasmid pBRHtrp was digested with EcoRI. restriction enzyme and the resulting fragment, isolated by PAGE and electroelution, was combined with EcoRIdigested plasmid pSOM11 (Itakura et al., 1977, Sci. 198:1056, G. B. Patent Publication No. 2,007,676A).

The mixture was ligated with $T_4$ DNA ligase and the resulting DNA transformed into *E. coli* K12 294 as previously described. Transformant bacteria were selected on ampicillin-containing plates and the resulting ampicillin-resistant colonies were screened by colony hybridization (Gruenstein et al., 1975, Proc. Nat. Acad. Sci. USA 72:3951-3965). The trp promoter/operator-containing fragment, isolated from pBRH trp and then radioactively labelled with $^{32}p$, was used as a probe in the above procedure. Several colonies were shown to be positive by colony hybridization and were therefore selected. Plasmid DNA was isolated and the orientation of the inserted fragments was determined by restriction analysis, using enzymes BglII and BamHI in double digestion. Colonies containing the desired plasmid with the trp promoter/operator fragment in the proper orientation were grown in LB medium (Miller, 1972) containing 10 μg./ml. ampicillin. The desired plasmid was designated pSOM7Δ2 and was used for subsequent constructions described below.

D. Construction of Plasmid pTrp24

1. Construction of a Gene Fragment Comprising Codons for the Distal Regions of the LE' Polypeptide With BglII and EcoRI Restriction Sites Respectively at the 5' and 3' Ends of the Coding Strand Plasmid pSOM7Δ2 was HindIII digested followed by digestion with lambda exonuclease (a 5' to 3' exonuclease) nuclease) under conditions chosen so as to digest beyond the BglII restriction site within the LE' encoding region. About 20 μg. of HindIII-digested pSOM7Δ2 was dissolved in buffer (20 mM glycine buffer, pH 9.6, 1 mM $MgCl_2$, 1 mM β-mercaptoethanol). The resulting mixture was treated with 5 units of lambda exonuclease for 60 minutes at room temperature. The reaction mixture obtained was then phenol extracted, chloroform extracted, and ethanol precipitated.

To create an EcoRI residue at the distal end of the LE' gene fragment, a primer $^{32}$pCCTGTGCATGAT was synthesized by the improved phosphotriester method (Crea et al., 1978, Proc. Nat. Acad. Sci. USA 75: 5765) and hybridized to the single stranded end of the LE' gene fragment resulting from lambda exonuclease digestion. The hybridization was performed by dissolving 20 μg. of the lambda exonuclease-treated HindIII digestion product of plasmid pSOM7Δ2 in 20 μl. $H_2O$ and combining with 6 μl. of a solution containing approximately 80 picomoles of the 5'-phosphorylated oligonucleotide described above. The synthetic fragment was hybridized to the 3' end of the LE' coding sequence and the remaining single strand portion of the LE' fragment was filled in by Klenow Polymerase I using dATP, dTTP, dGTP and dCTP. Klenow Polymerase I is the fragment obtained by proteolytic cleavage of DNA Polymerase I. It contains the 5'→3' polymerizing activity, the 3'→5' exonucleolytic activity, but not the 5'→3' exonucleolytic activity of the parental enzyme (Kornberg, 1974, W. H. Freeman and Co., SFO, 98).

The reaction mixture was thus heated to 50° C. and let cool slowly to 10° C., whereafter 4 μl. of Klenow enzyme were added. After 15 minutes incubation at room temperature, followed by 30 minutes incubation at 37° C., the reaction was stopped by the addition of 5 μl. of 0.25 molar EDTA. The reaction mixture was phenol extracted, chloroform extracted, and ethanol precipitated. The DNA was subsequently cleaved with the restriction enzyme BglII and the fragments were separated by PAGE. An autoradiogram obtained from the gel revealed a $^{32}$P-labelled fragment of the expected length of approximately 470 bp, which was recovered by electroelution. As outlined, this fragment LE' (d) has a BglII terminus and a blunt end coinciding with the beginning of the primer.

2. Construction of Plasmid pThaI

Plasmid pThaI was constructed by inserting a synthesized gene for thymosin alpha 1 into plasmid pBR322. The synthesis of the thymosin alpha 1 coding DNA involves the synthesis and subsequent ligation of the 16 oligonucleotides ($T_1$ through $T_{16}$) that are indicated by the double headed arrows in FIG. 7 of the accompanying drawings. A Met codon ATG was inserted at the N-terminus and the 5' ends were designed with single-stranded cohesive termini to facilitate joining to plasmids cleaved with EcoR1 and BamH1. As can be readily appreciated, the BglII site in the center of the gene assists in the analysis of recombinant plasmids.

Oligodeoxyribonucleotides $T_1$ to $T_{16}$ were synthesized by the modified phosphotriester method using fully protected trideoxyribonucleotide building blocks (Itakura et al., 1977, Science 198:1056, and Crea et al., 1978). The various oligodeoxyribonucleotides are shown below in Table 1.

TABLE 1

| \multicolumn{4}{c}{SYNTHETIC OLIGONUCLEOTIDES FOR THYMOSINα1 GENE} |

| Compound | Sequence | Length | HPLC Analysis Retention Time (min)* |
|---|---|---|---|
| $T_1$ | A-A-T-T-C-A-T-G-T-C | 10 | 17.4 |
| $T_2$ | T-G-A-T-G-C-T-G-C-T-G-T-T-G-A | 15 | 24.3 |
| $T_3$ | T-A-C-T-T-C-T-T-C-T-G-A | 12 | 20.3 |
| $T_4$ | G-A-T-T-A-C-T-A-C-T-A-A-A | 13 | 22.0 |
| $T_5$ | G-C-A-G-C-A-T-C-A-G-A-C-A-T-G | 15 | 24.8 |
| $T_6$ | G-A-A-G-T-A-T-C-A-A-C-A | 12 | 20.1 |
| $T_7$ | A-G-T-A-A-T-C-T-C-A-G-A-A | 13 | 22.6 |
| $T_8$ | A-A-G-A-T-C-T-T-T-A-G-T | 12 | 20.2 |

TABLE 1-continued
SYNTHETIC OLIGONUCLEOTIDES FOR THYMOSINα1 GENE

| Compound | Sequence | Length | HPLC Analysis Retention Time (min)* |
|---|---|---|---|
| $T_9$ | G-A-T-C-T-T-A-A-G-G-A-G | 12 | 20.4 |
| $T_{10}$ | A-A-G-A-A-G-G-A-A-G-T-T | 12 | 21.1 |
| $T_{11}$ | G-T-C-G-A-A-G-A-G-G-C-T | 12 | 20.5 |
| $T_{12}$ | G-A-G-A-A-C-T-A-A-T-A-G | 12 | 20.4 |
| $T_{13}$ | C-T-T-C-T-T-T-C-T-C-C-T-T | 12 | 19.9 |
| $T_{14}$ | T-T-C-G-A-C-A-A-C-T-T-C | 12 | 20.5 |
| $T_{15}$ | G-T-T-C-T-C-A-G-C-C-T-C | 12 | 20.2 |
| $T_{16}$ | G-A-T-C-C-T-A-T-T-A | 10 | 17.2 |

*at ambient temperature

Figure 8:
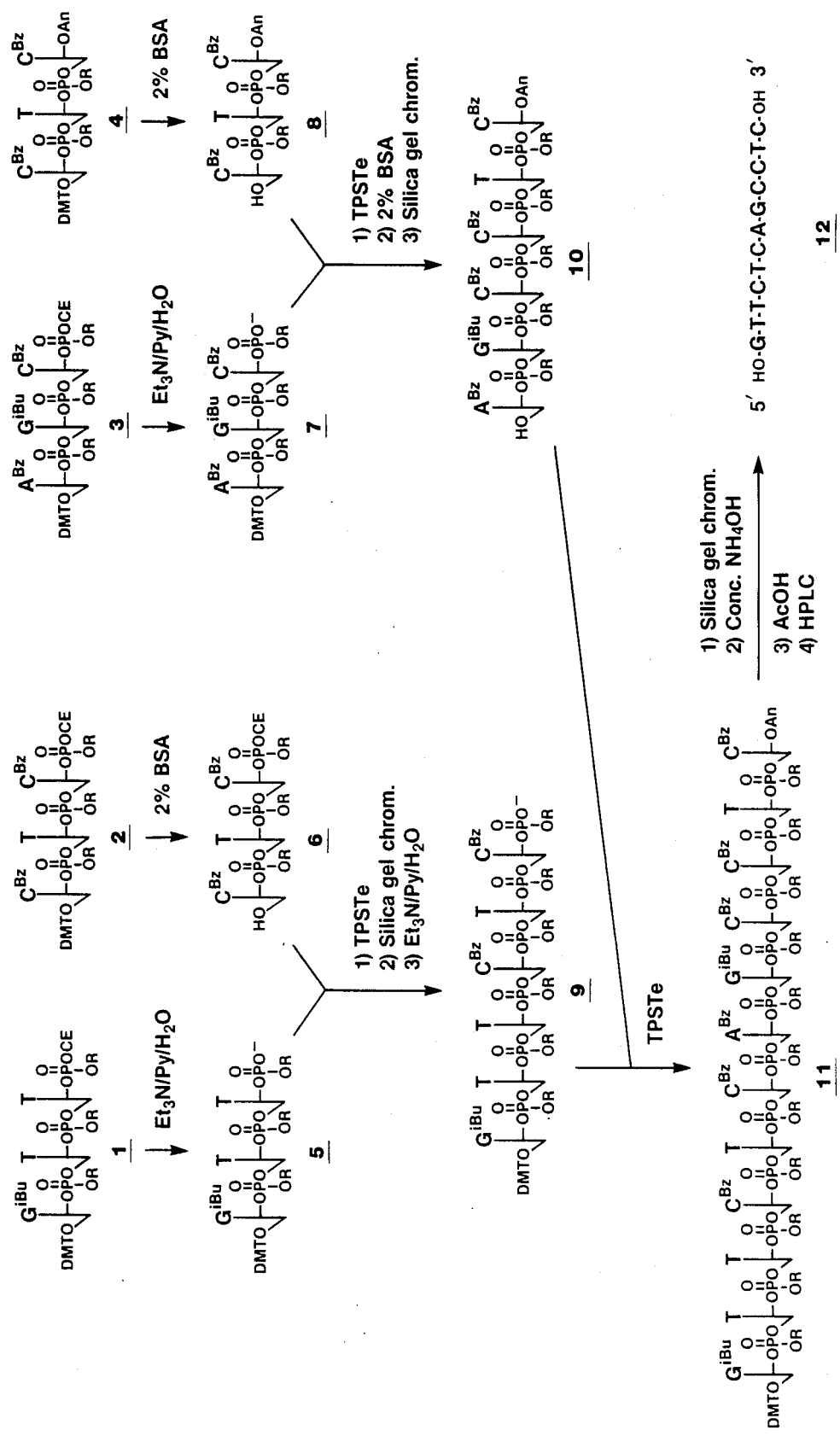
FIG. 8 depicts the synthesis procedure for fragment T$_{15}$.

The above synthesis is typified by the following procedure for fragment $T_{15}$ as summarized in FIG. 8 of the accompanying drawings. Various nucleotide fragments that are used in the synthesis of $T_{15}$ are numerically designated in the Figure. The abbreviations employed are as follows: TPSTe, 2,4,6-triisopropylbenzenesulfonyltetrazole; BSA, benzene sulfonic acid; TLC, thin layer chromatography; HPLC, high performance liquid chromatography; DMT, 4,4'-dimethoxytrityl; CE, 2-cyanoethyl; R, p-chlorophenyl; Bz, benzoyl; An, anisoyl; iBu, isobutryl; Py, pyridine; AcOH, acetic acid; Et$_3$N, triethylamine.

The fully protected trideoxyribonucleotides 4 (85 mg., 0.05 mmol) and 2 (180 mg., 0.1 mmol) were deblocked at the 5' hydroxyls by treatment with 2% BSA in 7:3 (v/v) chloroform/methanol (10 and 20 ml., respectively) for 10 minutes at 0° C. Reactions were stopped by addition of saturated aqueous ammonium bicarbonate (2 ml.), extracted with chloroform (25 ml.) and washed with water (2×10 ml.). The organic layers were dried (magnesium sulfate), concentrated to small volumes (about 5 ml.) and precipitated by addition of petroleum ether (35°-60° C. fraction). The colorless precipitates were collected by centrifugation and dried in a dessicator in vacuo to give 6 and 8, respectively, each homogeneous by silica gel tlc (Merck 60 F254, chloroform/methanol, 9:1).

Trimers 1 and 3 (270 mg., 0.15 mmol; 145 mg., 0.075 mmol) were converted into their phosphodiesters (5 and 7) by treatment with triethylamine/pyridine/water (1:3:1, v/v, 10 ml.) for 25 minutes at ambient temperature. Reagents were removed by rotary evaporation and the residues dried by repeated evaporations with anhydrous pyridine (3×10 ml.). Trimer 8 (0.05 mmol) and trimer 7 were combined with TPSTe (50 mg., 0.15 mmol) in anhydrous pyridine (3 ml.) and the reaction mixture left in vacuo at ambient temperature for two hours. TLC analysis showed that 95% of the trimer 8 had been converted into hexamer product (visualized by detection of the DMT group by spraying with 10% aqueous sulfuric acid and heating at 60° C.). The reaction was quenched by addition of water (1 ml.) and the solvent evaporated under reduced pressure. After removal of pyridine by coevaporations with toluene, the hexamer was deblocked at the 5' position with 2% BSA (8 ml.) as described above for trimers 4 and 2. The product (10) was purified on a silica gel column (Merck 60 H, 3.5×5 cm.) by step gradient elution with chloroform/methanol (98:2 to 95:5, v/v). Fractions containing product 10 were evaporated to dryness.

Similarly, trimer 5 was coupled to 6 and the fully protected product directly purified on silica gel. This latter compound was deblocked at the 3' end by triethylamine/pyridine/water as described above to give fragment 9.

Finally, hexamers 9 and 10 were coupled in anhydrous pyridine (2 ml.) with TPSTe (75 mg., 0.225 mmol) as the condensing agent. Upon completion (4 hours, ambient temperature) the mixture was rotary evaporated and the residue chromatographed on silica gel. Product 11 (160 mg.) was obtained by precipitation with petroleum ether and appeared homogeneous on TLC. A portion of compound 11 (20 mg.) in pyridine 0.5 ml.) was completely deblocked by treatment with concentrated ammonium hydroxide (7 ml., 8 hours, 60° C.) and subsequent treatment in 80% acetic acid (15 minutes, ambient temperature). After evaporation of acetic acid, the solid residue was dissolved in 4% aqueous ammonium hydroxide (v/v, 4 ml.) and extracted with ethyl ether (3×2 ml.). The aqueous phase was concentrated to 1-2 ml. and a portion applied to HPLC for purification of 12. The fractions corresponding to the major peak were pooled (ca. 2 O.D.$_{254}$ units) and concentrated to about 5 ml. The final product 12 was desalted on Bio-gel P-2 (1.5×100 cm.) by elution with 20% aqueous ethanol, reduced to dryness and resuspended in water (200 μl.) to give a solution of $A_{254} = 10$. The sequence of 12 was confirmed by two-dimensional sequence analysis.

Figure 9:
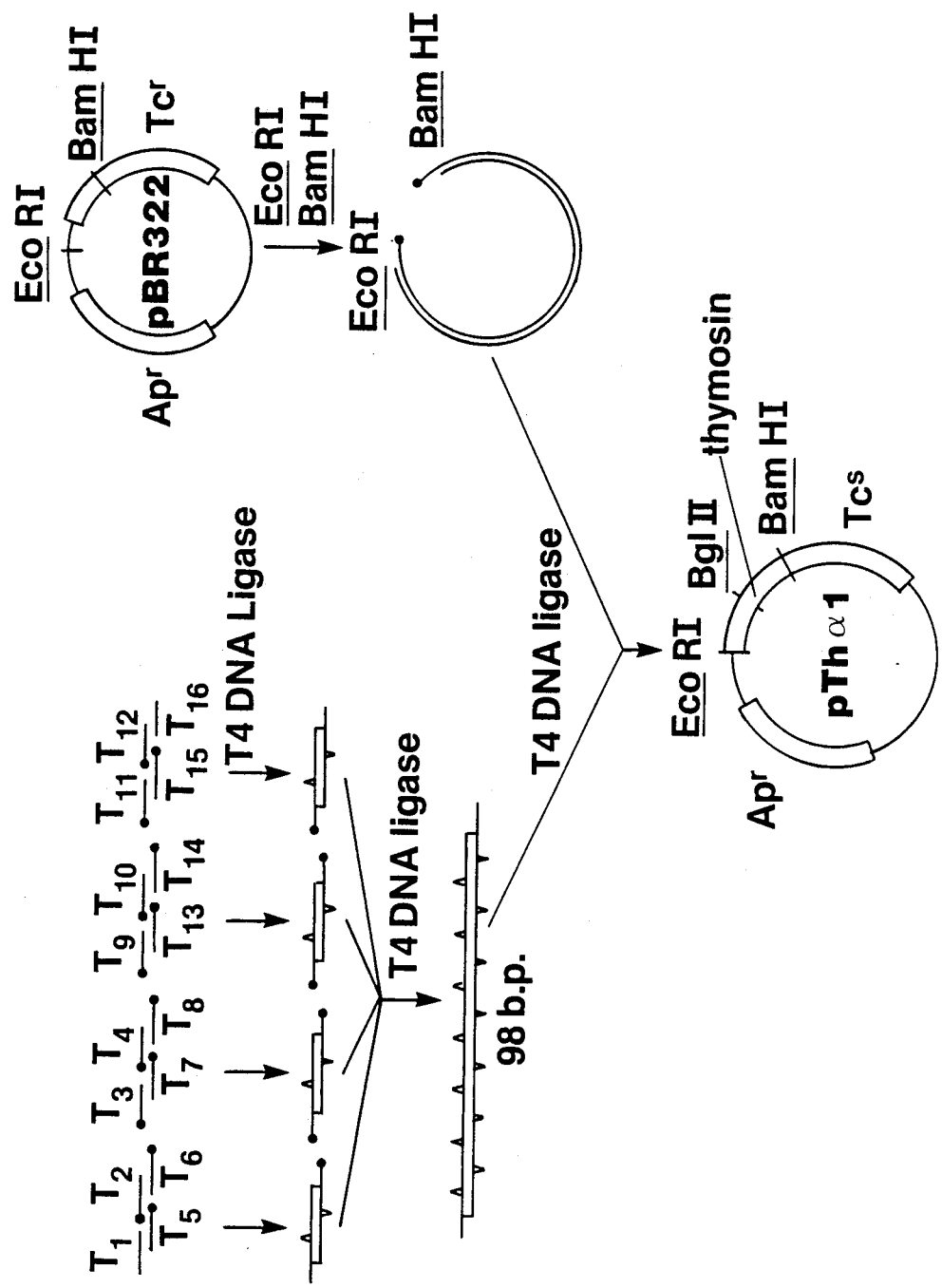
FIG. 9 depicts the construction route for plasmid pThα1.

The complete thymosin alpha 1 gene was assembled from the 16 synthetic oligo-nucleotides by methods previously described in detail for somatostatin (Itakura et al., 1977), insulin (Goeddel et al., 1979), and growth hormone (Goeddel, Heyneker, et al., 1979, Nature 281:544). Ten microgram quantities of oligonucleotides $T_2$ through $T_{15}$ were quantitatively phosphorylated with [γ-$^{32}$P]-ATP (New England Nuclear) in the presence of $T_4$ polynucleotide kinase (Goeddel et al, 1979), to give specific activities of approximately 1 Ci/mmol. Radio-labelled fragments were purified by 20% polyacrylamide/7 M urea gel electrophoresis and sequences of the eluted fragments were verified by two-dimensional electrophoresis/homochromatography (Jay et al., 1974, Nucleic Acids Res. 1:331) of partial snake venom digests. Fragments $T_1$ and $T_{16}$ were left unphosphorylated to minimize undesired polymerization during subsequent ligation reactions. These oligonucleotides (2 μg. each) were assembled in four groups of four fragments (see FIG. 9 of the accompanying drawings), by $T_4$ DNA ligase using published procedures (Goeddel et al., 1979). The reaction products were purified by gel electrophoresis on a 15% polyacrylamide gel containing 7 M urea (Maxam and Gilbert, 1977, Proc. Nat. Acad. Sci. USA 71:3455). The four isolated products were ligated together and the reaction mixture resolved by 10% polyacrylamide gel electrophoresis. DNA in the size range of the thymosin alpha 1 gene (90-105 base pairs) was electroeluted.

Plasmid pBR322 (0.5 μg.) was treated with BamHI and EcoRI restriction endonucleases and the fragments separated by polyacrylamide gel electrophoresis. The large fragment was recovered from the gel by electroelution and subsequently ligated to the assembled synthetic DNA (Goeddel, Heyneker, et al., 1979). This mixture was used to transform E. coli K12 294. Five percent of the transformation mixture was plated on LB plates containing 20 μg./ml. ampicillin. The four ampicillin resistant colonies obtained were sensitive to tetracycline, suggesting insertion into the tetracycline resistance gene. Analysis of the plasmids from these four colonies showed that in each case the plasmid, designated pThα1, contained (a) a BglII site not found in pBR322 itself, thus indicating the presence of the thymosin alpha 1 gene as shown in FIG. 7, and (b) a fragment of approximately 105 base pairs generated by BamHI/EcoRI cleavage. The construction route for plasmid pThα1 (not drawn to scale), is presented in FIG. 9 of the accompanying drawings wherein the heavy dots indicate 5'-phosphate groups.

3. Reaction of Treated pThα1 and LE' (d) Fragment

The plasmid pThα1 contains a gene specifying ampicillin resistance and a structural gene specifying thymosin alpha 1 cloned at its 5' coding strand end into an EcoRI site and at its 3' end into a BamHI site. The thymosin gene contains a BglII site as well. To create a plasmid capable of accepting the LE' (d) fragment prepared above, pTHα1 was EcoRI digested followed by Klenow polymerase I reaction with dTTP and dATP to blunt the EcoRI residues. BglII digestion of the resulting product created a linear DNA fragment containing the gene for ampicillin resistance and, at its opposite ends, a sticky BglII residue and a blunt end. The resulting product could be recircularized by reaction with the LE' (d) fragment containing a BglII sticky end and a blunt end in the presence of T4 ligase to form the plasmid pTrp24. In doing so, an EcoRI site is recreated at the position where blunt end ligation occurred.

E. Construction of Plasmid pSOM7Δ2Δ4

Successive digestion of pTrp24 with BglII and EcoRI, followed by PAGE and electroelution, yields a fragment having codons for the LE' (d) polypeptide with a BglII sticky end and an EcoRI sticky end adjacent to its 3' coding terminus. The LE' (d) fragment can be cloned into the BglII site of plasmid pSom7Δ2 to form an LE' polypeptide/somatostatin fusion protein expressed under the control of the tryptophan promoter/operator. To do so requires (1) partial EcoRI digestion of pSom7Δ2 in order to cleave the EcoRI site distal to the tryptophan promoter/operator, and (2) proper choice of the primer sequence in order to properly maintain the codon reading frame, and to recreate an EcoRI cleavage site.

Thus, 16 μg. of plasmid pSom7Δ2 were diluted into 200 μl. of buffer containing 20 mM Tris, pH 7.5, 5 mM MgCl2, 0.02% NP40 detergent, and 100 mM NaCl, and treated with 0.5 units EcoRI. After 15 minutes at 37° C., the reaction mixture was phenol extracted, chloroform extracted, ethanol precipitated, and subsequently digested with BglII. The larger resulting fragment was isolated by the PAGE procedure followed by electroelution. This fragment contains the codons "LE' (p)" for the proximal end of the LE' polypeptide, ie, those upstream from the BglII site. This fragment was next ligated to the above LE'(d) fragment in the presence of T4 DNA ligase to form the plasmid pSom7Δ2Δ4, which upon transformation into E. coli 294, efficiently produced a fusion protein consisting of the fully reconstituted LE polypeptide and somatostatin under the control of the tryptophan promoter/operator.

F. Construction of Linear DNA Having a PstI Residue at the 3' end and a BglII Residue at its 5' End Bounding a Gene Specifying Tetracycline Resistance Plasmid pBR322 was HindIII digested and the protruding HindIII ends were digested with S1 nuclease. The S1 nuclease digestion involved treatment of 10 μg. of HindIII-cleaved pBR322 in 30 μl. S1 buffer (0.3M NaCl, 1 mM ZnCl2, 25 mM sodium acetate, pH 4.5) with 300 units S1 nuclease for 30 minutes at 15° C. The reaction was stopped by the addition of 1 μl. of 30X S1 nuclease stop solution (0.8M tris base, 50 mM EDTA). The mixture was phenol extracted, chloroform extracted, ethanol precipitated, and then EcoRI digested as previously described. The resulting fragment, obtained by the PAGE procedure followed by electroelution, has an EcoRI sticky end and a blunt end whose coding strand begins with the nucleotide thymidine. The S1-digested HindIII residue beginning with thymidine can be joined to a Klenow Polymerase I-treated BglII residue so as to reconstitute the BglII restriction site upon ligation.

Therefore plasmid pSOM7Δ2, prepared in Example 2C, was BglII digested and the resulting BglII sticky ends were made double stranded by treatment with Klenow Polymerase I using all four deoxynucleotide triphosphates. EcoRI cleavage of the resulting product, followed by PAGE and electroelution of the small fragment, yielded a linear piece of DNA containing the tryptophan promoter/operator and codons of the LE' "proximal" sequence upstream from the BglII site ("LE'(p)"). The product had an EcoRI end and a blunt end resulting from filling in the BglII site. However, the BglII site is reconstituted by ligation of the blunt end to the blunt end of the above S1-digested HindIII fragment. Thus, the two fragments were ligated in the presence of T4 DNA ligase to form the recircularized plasmid pHKY10 which was propagated by transformation into competent E. coli 294 cells. Tetracycline resistant cells bearing the recombinant plasmid pHKY10 were selected and the plasmid DNA extracted. Digestion with BglII and PstI, followed by isolation by the PAGE procedure and electroelution of the large fragment, yielded the desired linear piece of DNA having PstI and BglII sticky ends. This DNA fragment, thus produced from pHKY10, contains the origin of replication and therefore is useful as a component in the construction of plasmid pIA7Δ4Δ1 in which both the genes coding for the trp LE' polypeptide fusion protein and the tetracycline resistance are controlled by the trp promoter/operator.

G. Construction of Linear DNA Having the Trp Promoter/Operator

Plasmid pSOM7Δ2Δ4, prepared in Example 2E, was subjected to partial EcoRI digestion followed by PstI digestion. The resulting fragment contained the trp promoter/operator and was isolated by the PAGE procedure followed by electroelution. Partial EcoRI digestion was necessary to obtain a fragment which was cleaved adjacent to the 5' end of the somatostatin gene but not cleaved at the EcoRI site present between the ampicillin resistance gene and the trp promoter/operator. Ampicillin resistance lost by the PstI cut in the ampicillin resistance gene can be restored upon ligation with the final pHKY10 linear DNA derivative produced in Example 2F above.

H. Isolation of the Insulin A Chain Structural Gene

The insulin A chain structural gene was obtained by the EcoRI and BamHI digestion of plasmid pIA1, whose construction is disclosed in Goeddel et al., 1979, Proc. Nat. Acad. Sci. USA 76:106. The desired fragment was purified by PAGE and electroelution and had EcoRI and BamHI termini.

I. Ligation of the Insulin A Chain Structural Gene, the Trp Promoter/Operator, and the pHKY10 Linear DNA Fragment Having PstI and BglII Termini The Insulin A Chain structural gene, the linear DNA fragment containing the trp promoter/operator (prepared in Example 2G), and the pHKY10 linear DNA fragment (prepared in Example 2F), were ligated together in the orientation depicted in FIG. 1, to form the desired plasmid pIA7Δ4Δ1. Plasmid pIA7Δ4Δ1 can be readily selected because of the restoration of ampicillin and tetracycline resistance.

Example 3

Construction of Plasmid pIB7Δ4Δ1

The desired plasmid was constructed in accordance with Example 2A-I except that the structural gene specifying the insulin B chain, rather than the insulin A chain, was used in the final ligation. The insulin B chain structural gene was obtained by the EcoRI and BamHI digestion of plasmid pIB1, whose construction is disclosed in Goeddel et. al., 1979. The insulin B chain encoding DNA fragment was purified by PAGE and electroelution and had EcoRI and BamHI termini.

Figure 3:
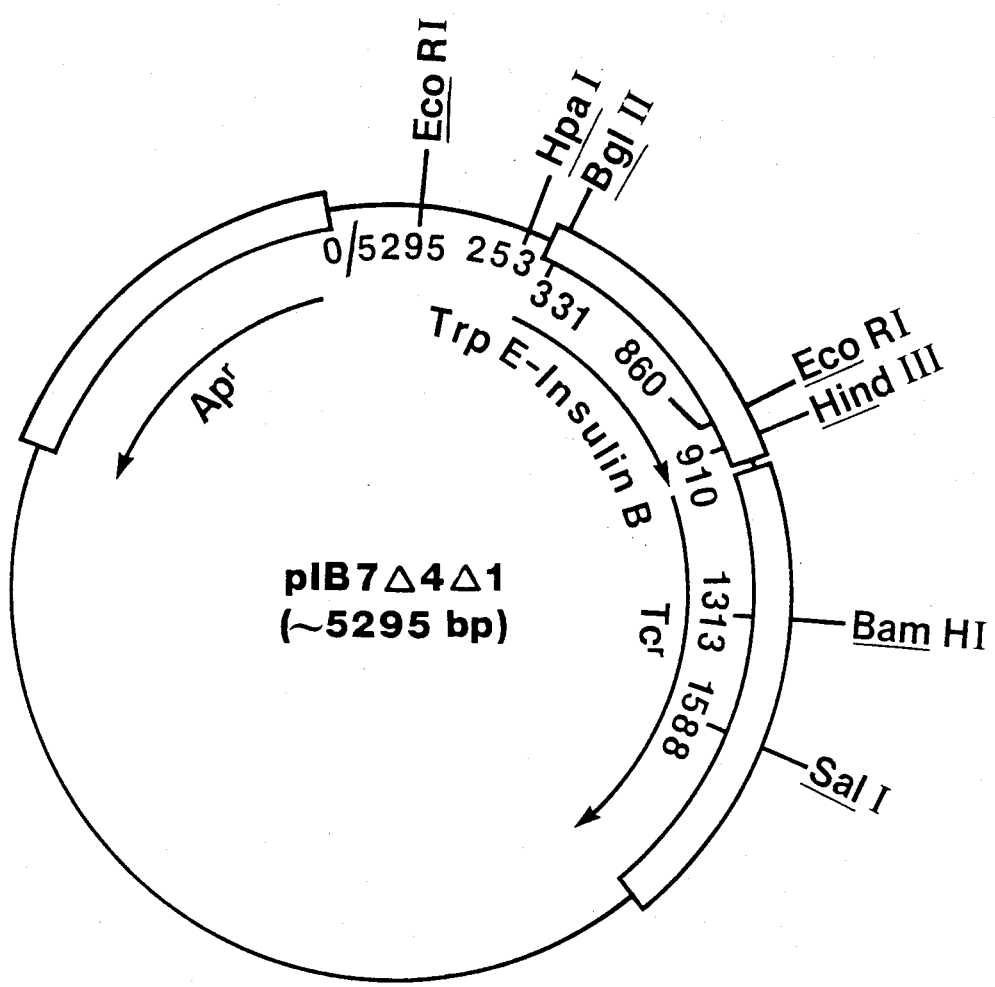
FIG. 3 is a restriction site and function map of plasmid pIB7Δ4Δ1.
Figure 4:
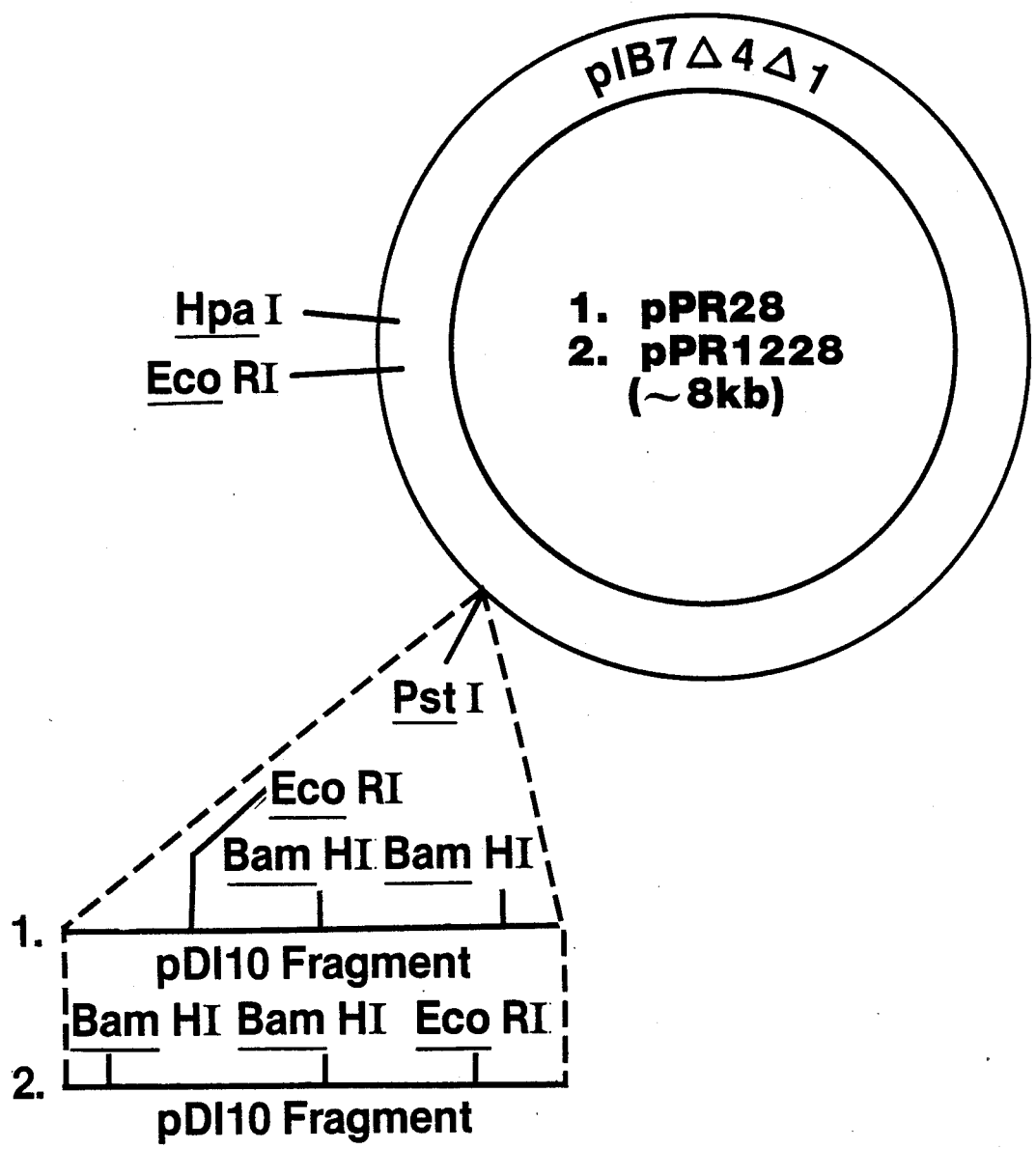
FIG. 4 is a restriction site map of plasmids pPR28 and pPR1228.

Plasmid pIB7Δ4Δ1 is depicted in FIG. 3 and can be readily selected because of the restoration of ampicillin and tetracycline resistance.

EXAMPLE 4

Construction of Plasmid pHI7Δ4Δ1

The scheme for construction of plasmid pHI7Δ4Δ1 is presented in FIG. 11 of the accompanying drawings.

A. Construction of Plasmid pSOM7Δ4Δ1

The desired construction is analogous to that presented in Example 2I. Thus, the linear DNA fragment containing the trp promoter/operator (prepared in Example 2G) and the pHKY10 linear DNA fragment (prepared in Example 2F) were conventionally ligated to the somatostatin gene-containing EcoRI-BamHI restriction fragment of plasmid pSOM11. Plasmid pSOM11 can be constructed in substantial accordance with the teaching of Itakura, et al., 1977, Science 198:1056 and G. B. Patent Publication No. 2007676A. The desired plasmid pSOM7Δ4Δ1 can be readily selected because of the restoration of ampicillin resistance.

B. Preparation of Synthetic Gene Coding for the 32 N-Terminal Amino Acids of Proinsulin A series of 18 oligonucleotides, shown in Table 2, were prepared as a first step in constructing a gene coding for the first 32 amino acids of proinsulin. The individual nucleotides are identified by the letters A, T, C or G representing the bases adenine, thymine, cytosine or guanine which distinguish one nucleotide from another. The nucleotide sequence of the entire gene ultimately constructed is shown in FIG. 10.

TABLE 2

| Synthetic Oligonucleotides For Proinsulin Gene | |
|---|---|
| Compound | Sequence |
| H1 | AATTCATGTT |
| H2 | CGTCAATCAGCA |
| H3 | CCTTTGTGGTTC |
| H4 | TCACCTCGTTGA |
| H5 | TTGACGAACATG |
| H6 | CAAAGGTGCTGA |
| H7 | AGGTGAGAACCA |
| H8 | AGCTTCAACG |
| B1 | AGCTTTGTAC |
| B2 | CTTGTTTGCGGT |
| B3 | GAACGTGGTTTC |
| B4 | TTCTACACTCCT |
| B5' | AAGACTCGCC |
| B6 | AACAAGGTACAA |
| B7 | ACGTTCACCGCA |
| B8 | GTAGAAGAAACC |
| B9 | AGTCTTAGGAGT |
| B10' | GATCCGGCG |

Figure 10:
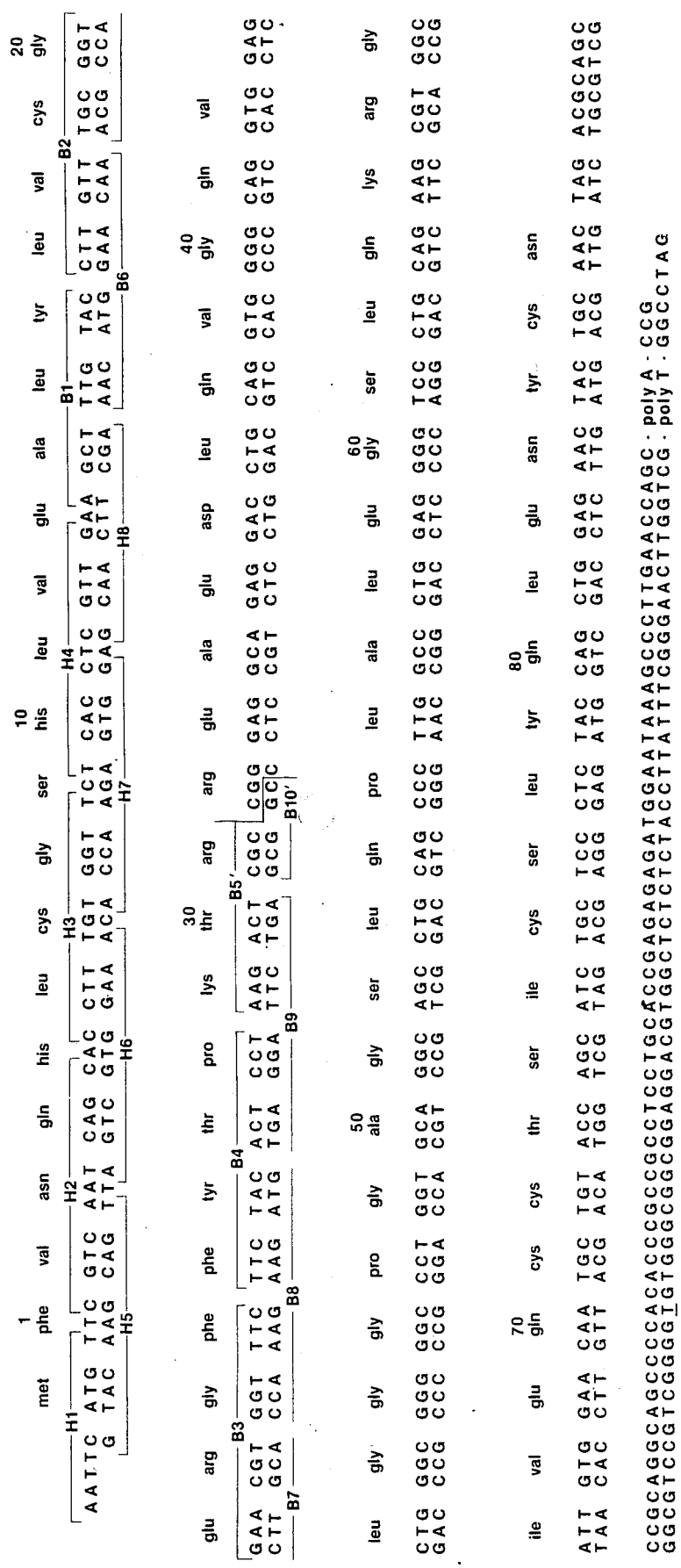
FIG. 10 depicts the DNA sequence and encoded amino acid residue sequence of a synthetic proinsulin gene.

The synthetic nucleotides are shown between brackets and are underlined in FIG. 10. These olignucleotides were synthesized by the triester method, Crea, et al., 1978, Proc. Nat. Acad. Sci., USA 75:5765, Itakura, et al., 1975, J. Biol. Chem. 250:4592, and Itakura, et al., 1975, J. Am. Chem. Soc. 97:7327. Some of the oligonucleotides were used for constructing a gene for the human insulin B chain previously described by Crea, et al., 1978 and Goeddel, et al, 1979. Two oligonucleotides (B5' and B10') incorporate HpaII and terminal BamHI and EcoRI restriction sites. The terminal sites are particularly useful for purposes of cloning.

The eight oligonucleotides H1-H8, used previously for constructing the left half of the human insulin B chain gene (Goeddel, et al., 1979), contain the codons for the 1-13 amino acids of the B chain gene and also a methionine unit at the N-terminus. The right half of the B chain gene was constructed from oligonucleotides $B_1$, $B_2$, $B_3$, $B_4$, $B_{5'}$, $B_6$, $B_7$, $B_8$, $B_9$ and $B_{10'}$ by ligation using T4 DNA ligase in substantial accordance with the teaching of Goeddel, et al., 1979. The resultant gene fragment codes for the 14-30 amino acid units of the human insulin B chain and the first arginine unit of the bridging chain. A HpaII restriction site is incorporated into the gene sequence in the same reading frame and location as the HpaII site in the human insulin gene. After purification of the ligated gene fragment by polyacrylamide gel electrophoresis and after elution of the largest DNA band, the fragment was inserted into HindIII-BamHI-cleaved plasmid pBR322. The resultant plasmid, designated pB3, was inserted into E. coli K12 294 (ATCC No. 31446) by transformation. The plasmid conferred resistance to antibiotics ampicillin and tetracycline and was found to contain the desired nucleotide sequence as determined by the method of Maxam, et al., 1977, Proc. Natl. Acad. Sci. USA 74:560.

Two fragments, a 58 base pair HindIII-BamHI fragment of pB3 and a 46 base pair EcoRI-HindIII fragment of pBH1 (disclosed in Goeddel, et al., 1979), were ligated to produce a fragment having EcoRI and BamHI termini. This fragment was ligated into EcoRI and BamHI restricted plasmid pBR322 in substantial accordance with the teaching of Goeddel, et al., 1979. The resultant plasmid, designated pIB3, was then cloned into E. coli K12 294. After conventional amplification and isolation, plastid pIB3 was digested with EcoRI and HpaII restriction enzyme to produce a synthetic gene fragment (Fragment 1, FIG. 11) that codes for the N-terminal proinsulin amino acids preceded by a methionine. The synthetic gene was isolated conventionally by polyacrylamide gel electrophoresis.

C. Isolation of cDNA Coding for the 50 C-Terminal Amino acids of Human Proinsulin The scheme for obtaining the desired cDNA is presented in FIG. 12 of the accompanying drawings. In accordance therewith, the decanucleotide pCCGGATCCGGTTT$_{18}$T, which contained both a BamHI recognition sequence and a 3' polythymidylic acid tract of approximately 20 residues, was synthesized and used to prime AMV reverse transcriptase for cDNA synthesis. The primer was prepared using terminal deoxynucleotidyl transferase (Enzo Biochem, 200 units) with 1 μmol of the BamHI decanucleotide in a reaction volume of 0.6 ml. containing $1.5 \times 10^{-4}$ μmol TTP. The reaction was conducted at 37° C. for 1 hour in the buffer system of Chang, et al., 1978, Nature 275:617.

Human insulinoma tissue was provided by the Institute für Diabetesforschung, Muenchen, West Germany. Those skilled in the art understand that human insulinoma tissue is readily available and can also be obtained from a number of other sources. Poly A mRNA (2.5 μg.) of the human insulinoma tissue was isolated in substantial accordance with the procedure of Ullrich, et al., 1977, Science 196:1313 and then converted to double stranded cDNA in substantial accordance with the teaching of Wickens, et al., 1978, J. Biol. Chem. 253:2483. Thus, a reaction volume of 80 μl. containing 15 mM Tris-HCl (pH 8.3 at 42° C.), 21 mM KCl, 8 14 MgCl$_2$, 30 mM B-mercaptoethanol, 2 mM of the primer dCCGGATCCGGTT$_{18}$T, and 1 mM dNTPs was preincubated at 0° C. After addition of AMV reverse transcriptase, the mixture was incubated for 15 minutes at 42° C. The resultant RNA/DNA was then denatured using conventional procedures.

The complementary cDNA strand was synthesized in a reaction volume of 150 μl. containing 25 mM Tris-HCl (pH 8.3), 35 mM KCl, 4 mM MgCl$_2$, 15 mM β-mercapto-ethanol 1 mM dNTPs and 9 units of DNA polymerase I (Klenow fragment). The mixture was incubated at 15° C. for 90 minutes followed by 15 hours at 4° C. S1 nuclease digestion was then performed for 2 hours at 37° C. using 1000 units of S1 nuclease (Miles Laboratories, Elkhart, Ind.) in substantial accordance with the teaching of Wickens, et al., 1978. The double stranded cDNA (0.37 μg) was electrophoresed on an 8% polyacrylamide gel' and DNA fragments larger than 500 base pairs were eluted. Oligodeoxycytidylic acid residues were added to the 3' ends of the fragments using terminal deoxynucleotidyl transferase in substantial accordance with the procedure of Maizel Jr., 1971, Meth. Virol. 5:180. The dC tailed cDNA fragments were then annealed to pBR322 that had first been digested with PstI restriction enzyme and then tailed with deoxyguanidylic acid using terminal deoxynucleotidyl transferase. The resulting plasmids were transformed into E. coli K12 294 and cloned. Colonies resistant to tetracycline but sensitive to ampicillin were isolated and screened for plasmids that had three PstI restriction sites. Such a restriction pattern is indicative of the gene for proinsulin, Sures, et al., 1980, Science 208:57.

One plasmid, pHI104, contained a 600 base pair insert, gave the anticipated PstI restriction pattern, and contained a BamHI site between the 3' polyA and the polyGC introduced during the cDNA preparation. Some of the nucleotide sequence of the insert is shown in FIG. 10. This sequence differs slightly (an AT [underlined]replaced a GC pair), from that previously reported by Sures, et al, 1980, and Bell, et al, 1979, Nature 282:525, because the mRNA used was from tissue isolated from a different individual.

D. Assembly of a Gene Coding for Human Proinsulin

The scheme used for assembling a gene coding for human proinsulin is shown in FIG. 11 of the accompanying drawings.

The synthetic gene segment coding for the first 31 amino acids of proinsulin, fragment 1 in FIG. 11, was recovered from 50 μg. of plasmid pIB3 using the restriction endonucleases EcoRI and HpaII as described above. This fragment also contains the codon ATG for methionine in place of the "presequence" of preproinsulin.

The cDNA gene segment coding for amino acids 32–86, as well as the translation stop codons and the 3' untranslated region of the mRNA, was recovered from 40 μg. of plasmid pHI104 by treatment first with BamHI and then HpaII restriction enzymes. The two fragments were isolated by polyacrylamide gel electrophoresis followed by electroelution. The gene fragments were joined by treatment with T4 DNA ligase in 20 μl. ligase buffer (Goeddel, et al., 1979), at 4° C. for 24 hours. The mixture was diluted with 50 μl. H$_2$O, conventionally extracted with each of phenol and chloroform and then precipitated with ethanol.

The resulting DNA was treated with BamHI and EcoRI restriction enzymes to regenerate these sites and remove gene polymers. The assembled proinsulin gene was isolated by polyacrylamide gel electrophoresis and ligated (using T4 DNA ligase) to EcoRI and BamHI digested plasmid pBR322. The resulting DNA was transformed into E. coli K12 294 and then the resultant colonies screened for tetracycline sensitivity and ampicillin resistance. Plasmid pHI3, isolated from one such colony, contained the desired proinsulin gene which was subsequently characterized by nucleotide sequence analysis.

E. Construction of a Plasmid for Expression of a Chimeric Protein Containing Human Proinsulin The complete human proinsulin gene, including the N-terminal codon that codes for methionine, was recovered from plasmid pHI3 by treatment with EcoRI and BamHI restriction enzymes. The desired fragment was purified by gel electrophoresis and then ligated (using T4 DNA ligase) to the PstI-EcoRI (partial) digest of plasmid pSOM7Δ4Δ1 and the larger of the PstI-BglII fragments of plasmid pHKY10 (prepared in Example 2F).

The pSOM7Δ4Δ1 fragment was constructed by partial EcoRI digestion followed by complete PstI digestion. The resulting fragment contained the trp promoter/operator and was isolated by PAGE followed by electroelution. Partial EcoRI digestion was necessary to obtain a fragment which was cleaved adjacent to the 5' end of the somatostatin gene but not cleaved at the EcoRI site between the ampicillin resistance gene and the trp promoter/operator. Ampicillin resistance, lost by the PstI cut in the ampicillin resistance gene, can be restored upon ligation with the final pHKY10 linear DNA derivative produced in Example 2F above.

About 1 μg. of the complete human proinsulin gene with EcoRI and BamHI termini, 4 μg. of PstI-EcoRI (partial) pSOM7Δ4Δ1 fragment, and about 1 μg of the PstI-BglII fragment of pHKY10 were ligated at 4° C. for 24 hours using T4 DNA ligase in ligation buffer.

Figure 5:
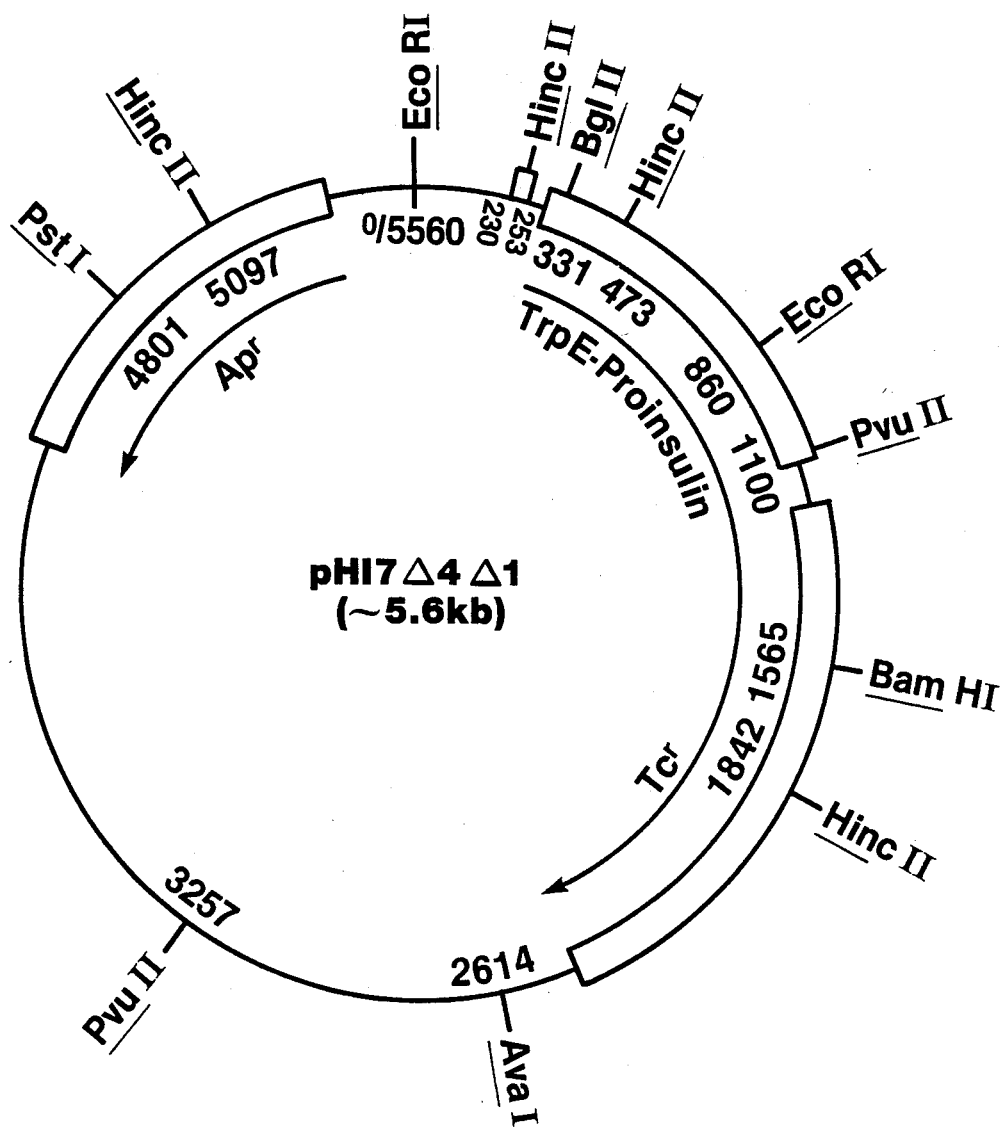
FIG. 5 is a restriction site and function map of plasmid pHI7Δ4Δ1.
Figure 6:
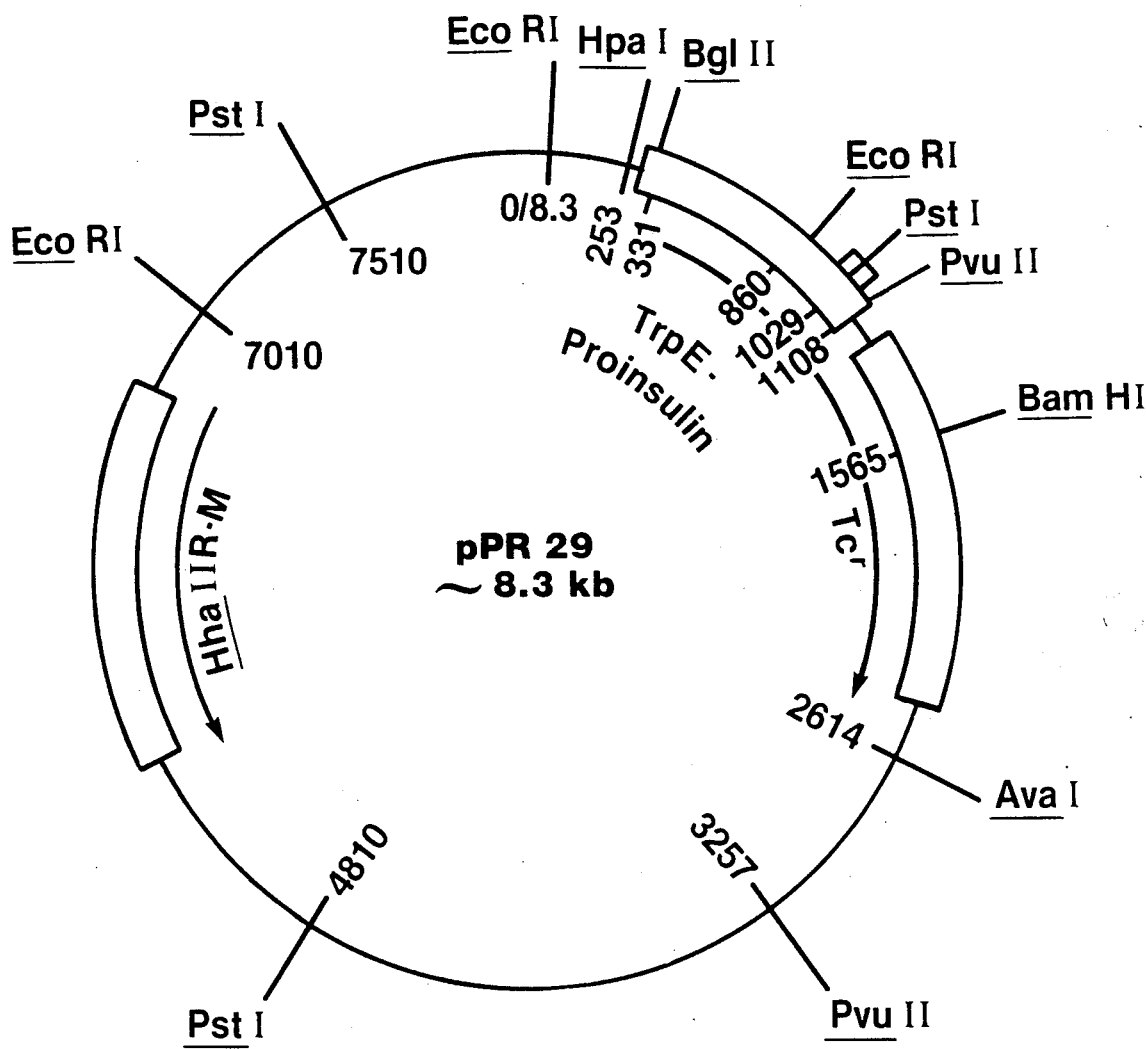
FIG. 6 is a restriction site and function map of plasmid pPR29.

The ligated DNA mixture was transformed into *E. coli* K12 294 in substantial accordance with the procedure of Goeddel, et al, 1979. Colonies that grew on both ampicillin and tetracycline were selected and were found by SDS polyacrylamide gel electrophoresis, Maizel, Jr., 1971, to contain the desired plasmid pHI7Δ4Δ1 and to express a protein of the molecular weight expected of the trp LE'-proinsulin fusion. Plasmid pHI7Δ4Δ1, which expressed the aforementioned protein, was completely characterized as to the DNA sequence and restriction sites of both the incorporated gene and also the vector. Plasmid pHI7Δ4Δ1 is depicted in FIG. 5 of the accompanying drawings and can be readily selected because of the restoration of ampicillin and tetracycline resistance.

EXAMPLE 5

Isolation of the ~2.7 kb PstI Fragment of pDI10

The ~2.7 kb PstI fragment of plasmid pDI10 contains genes for restriction and modification with the specificity of HhaII. About 15 µg. of covalently closed circular pDI10 isolated from *E. coli* K12 294/pDI10 were digested to completion at 37° C. with PstI restriction enzyme. The reaction mixture contained about 35 µl. of pDI10-solution (prepared in Example 1), 15 µl. of 10X PstI buffer (100 mM MgCl$_2$, 500 mM (NH$_4$)$_2$SO$_4$, and 200 mM Tris-HCl, pH 7.5), 15 µl. of Bovine Serum Albumin (1 mg./ml.), 77.5 µl. of H$_2$O, and 17.5 µl. of PstI restriction enzyme (1 New England Biolabs unit/µl.). The restricted DNA was fractionated by AGE (agarose gel electrophoresis) in gels containing 0.8% agarose in TBE (10.8 gm. Tris base, 5.5 gm. boric acid, and 0.09 gm. Na$_2$EDTA in 1 liter of H$_2$O) for 1.5 hr. at 220 volts. The bands were visualized by staining with ethidium bromide (0.5 µg./ml.) and observation under an ultraviolet light. The desired fragment was excised and electroeluted into TBE for 1 hr. at 150 volts. The DNA was bound to a DE.AE cellulose (Whatman DE52) column that had been equilibrated with equilibration buffer (0.1M KCl and 10 mM Tris-HCl, pH 7.8). The column was washed with equilibration buffer and DNA was eluted with elution buffer (1 M NaCl and 10 mM Tris-HCl, pH 7.8). The eluent was adjusted with H$_2$O to approximately 0.35 M with respect to Na$^+$ ion concentration and then the DNA was precipitated by addition of two volumes of 100% ethanol and cooling to −20° C. overnight. The desired precipitate was collected by centrifugation, dried, and dissolved in TE.

Example 6

Isolation of PstI Digested Plasmid pIA7Δ4Δ1

About 0.5 µg. of plasmid pIA7Δ4Δ1, prepared in Example 2, was digested for 3 hours at 37° C. with PstI restriction enzyme in substantial accordance with the procedure of Example 5. The restricted DNA was extracted once with phenol and twice with chloroform-:isoamyl alcohol (24:1) by standard procedures. The solution was mixed with 0.1 volume of 3 M sodium acetate, pH 8 and precipitated by addition of 2.2 volumes of ethanol and cooling to −20° C. overnight. The desired precipitate was collected by centrifugation, dried, and dissolved in TE.

EXAMPLE 7

Isolation of PstI Digested Plasmid pIB7Δ4Δ1

About 0.5 µg. of plasmid pIB7Δ4Δ1, prepared in Example 3, was digested for 3 hours at 37° C. with PstI restriction enzyme in substantial accordance with the procedure of Example 5. The restricted DNA was extracted once with phenol and twice with chloroform-:isoamyl alcohol (24:1) by standard procedures. The solution was mixed with 0.1 volume of 3 M sodium acetate, pH 8, and precipitated by addition of 2.2 volumes of 100% ethanol and cooling to −20° C. overnight. The desired precipitate was collected by centrifugation, dried, and dissolved in TE.

EXAMPLE 8

Ligation of the ~2.7 kb PstI Fragment of Plasmid pDI10 to the PstI Digested Plasmid pIA7Δ4Δ1

About 0.2 µg. of PstI digested plasmid pIA7Δ4Δ1 and 1.1 µg. of the ~2.7 kb PstI fragment of plasmid pDI10 were mixed in 400 µl. of TE/10 (1 mM Tris-HCl, pH7.8, 0.1 mM Na$_2$EDTA). After the addition of 0.1 volume of 3 M sodium acetate, pH 8, the DNA was precipitated by addition of 2.2 volumes of 100% ethanol and cooling to −20° C. overnight. The desired precipitate was collected by centrifugation and then dried. Ligation was performed in a 3.3 µl. reaction volume containing 2 µl. of DNA in H$_2$O, 0.6 µl. of 5X kinase-ligase buffer (50 mM MgCl$_2$, 25 mM dithiothreitol, 250 mM Tris-HCl, pH 7.8, and 25% glycerol), 0.6 µl. of 0.66 mM ATP and 0.1 µl. of T4 DNA ligase (1 unit/µl.). The reaction mixture was incubated overnight at 15° C.

EXAMPLE 9

Ligation of the ~2.7 kb PstI Fragment of Plasmid pDI10 to the PstI Digested Plasmid pIB7Δ4Δ1

The desired ligation was carried out in substantial accordance with the teaching of Example 8 except that PstI digested plasmid pIB7Δ4Δ1, rather than plasmid pIA7Δ4Δ1, was used. The reaction mixture was incubated overnight at 15° C.

EXAMPLE 10

Construction of *E. coli* K12 RV308/pPR26 and *E. coli* K12 RV30S/pPR27 and Isolation of Plasmids pPR26 and pPR27

About 0.1 µg. of ligated DNA, prepared in Example 8, was diluted to a final volume of 50 µl. with SSC/10. The DNA was then transformed into competent *E. coli*. K12 RV308 in substantial accordance with the transformation procedure of Example 1. The desired *E. coli* K12 RV308/pPR26 and *E. coli* K12 RV308/pPR27 transformants were isolated by growth on L-agar containing tetracycline at 5 µg./ml. Isolates were tested to verify tetracycline resistance and ampicillin sensitivity. Appropriate colonies were used to isolate covalently closed circular plasmid DNA in substantial accordance with the isolation procedure of Bazaral and Helinski, 1968. The structure of the plasmids was verified by mapping the restriction endonuclease cleavage sites. Plasmids of two orientations were obtained because the ~2.7 kb PstI restriction fragment comprising the plasmids can be inserted in either direction. Consequently, both plasmids pPR26 and pPR27 and their respective transformants are isolated in the above procedure.

EXAMPLE 11

Construction of *E. coli* K12 RV308/pPR28 and *E. coli* K12 RV308/pPR1228 and Isolation of Plasmids pPR28 and pPR1228

The desired constructions were made in substantial accordance with the teaching of Example 10 except that ligated DNA prepared in Example 9, rather than Example 8, was used. The desired *E. coli* K12 RV308/pPR28 and *E. coli* K12 RV308/pPR1228 transformants are isolated and the structure of their respective plasmids verified by mapping the restriction endonuclease cleavage sites. Plasmids of two orientations are obtained because the ~2.7 kb PstI restriction fragment comprising the plasmids can be inserted in either direction. Consequently, both plasmids pPR28 and pPR1228 and their respective transformants are isolated in the above procedure.

EXAMPLE 12

Construction of *E. coli* K12 RV308/pPR29 and Isolation of Plasmid pPR29

A. Isolation of the ~6.2 kb AvaI-BglII fragment of Plasmid pPR27

Plasmid pPR27 contains a single BglII restriction site at about base-pair coordinate 331 and a single AvaI site at about coordinate 2334. About 8 μg. of plasmid pPR27 (prepared in Example 10) were digested to completion at 37° C. in a 150 μl. reaction containing 20 mM Tris-HCl, pH 7.4, 30 mM NaCl and 16 units of AvaI restriction enzyme (BRL, 2 units/μl.). Following the addition of 20 μl. of 10x BglII buffer (1 M Tris-HCl, pH 8.0, 50 mM $MgCl_2$ and 600 mM NaCl) 25 μl. of $H_2O$ and 5 μl. of BglII restriction enzyme (New England Biolabs, 1.6 units μl.) the reaction was incubated at 37° C. for 60 minutes and then at 65° C. for 5 minutes. The restricted DNA was fractionated by AGE and then the desired ~6.2kb fragment recovered in TE by electroelution and DEAE cellulose chromatography in substantial accordance with the procedure of Example 5.

B. Isolation of the ~2.3kb AvaI-BglII Fragment of Plasmid pHI7Δ4Δ1

Plasmid pHI7Δ4Δ1 contains a single BglII restriction site at about base-pair coordinate 331 and a single AvaI site at about coordinate 2614. About 15 μg. of plasmid pHI7Δ4Δ1, prepared in Example 4, were digested to completion with AvaI and BglII restriction enzymes in substantial accordance with the procedure in Example 12A above. The restricted DNA was fractionated by AGE and then the desired ~2.3kb fragment recovered in TE by electroelution and DEAE cellulose chromatography in substantial accordance with the procedure of Example 5.

C. Ligation of the ~6.2kb AvaI-BglII Fragment of Plasmid pPR27 to the ~2.3kb AvaI-BglII Fragment of Plasmid pHI7Δ4Δ1

About 2.3 μg. of the ~6.2kb AvaI-BglII fragment of plasmid $pPR_{27}$ (prepared in Example 12A) and about 0.85 μg. of the ~2.3 kb AvaI-BglII fragment of pHI7Δ4Δ1 (prepared in Example 12B) were mixed in 570 μof TE and ethanol precipitated in substantial accordance with the procedure of Example 8. The recovered DNA was ligated in a 10.1 μl. reaction containing 2 μl. of 5x kinase-ligase buffer, 2 μl. of 0.66 mM ATP, 6 μl. of $H_2O$ and 0.1 μl of T4 DNA ligase (1 unit/ul).

After the reaction mixture was incubated overnight at 9° C., the desired DNA was recovered according to known procedures.

D. Construction of *E. coli* K12 RV308/pPR29 and Isolation of Plasmid pPR29

The desired construction was made in substantial accordance with the teaching of Example 10 except that ligated DNA prepared in Example 12C, rather than Example 8, was used. The desired *E. coli* K12 RV308/pPR29 was isolated and the structure of the plasmid verified by mapping the restriction endonuclease cleavage sites.

Representative transformants that can be constructed in accordance with the foregoing teaching include the following listed below in Table 3.

TABLE 3

| | Representative Transformants |
|---|---|
| 1. | *E. coli* K12 294/pPR26 |
| 2. | *E. coli* K12 294/pPR27 |
| 3. | *E. coli* K12 294/pPR28 |
| 4. | *E. coli* K12 294/pPR1228 |
| 5. | *E. coli* K12 294/pPR29 |
| 6. | *E. coli* K12/pPR27 |
| 7. | *E. coli* K12 C600/pPR26 |
| 8. | *E. coli* K12 C600/pPR27 |
| 9. | *E. coli* K12 C600/pPR28 |
| 10. | *E. coli* K12 C600/pPR1228 |
| 11. | *E. coli* K12 C600/pPR29 |
| 12. | *E. coli*/pPR27 |
| 13. | *E. coli* K12 C600$R_k^-M_k^-$/pPR26 |
| 14. | *E. coli* K12 C600$R_k^-M_k^-$/pPR27 |
| 15. | *E. coli* K12 C600$R_k^-M_k^-$/pPR28 |
| 16. | *E. coli* K12 C600$R_k^-M_k^-$/pPR1228 |
| 17. | *E. coli* K12 C600$R_k^-M_k^-$/pPR29 |
| 18. | *E. coli* K12/pPR28 |
| 19. | *E. coli* K12 HB101/pPR26 |
| 20. | *E. coli* K12 HB101/pPR27 |
| 21. | *E. coli* K12 HB101/pPR28 |
| 22. | *E. coli* K12 HB101/pPR1228 |
| 23. | *E. coli* K12 HB101/pPR29 |
| 24. | *E. coli*/pPR28 |
| 25. | *E. coli* K12 BE827/pPR26 |
| 26. | *E. coli* K12 BE827/pPR27 |
| 27. | *E. coli* K12 BE827/pPR28 |
| 28. | *E. coli* K12 BE827/pPR1228 |
| 29. | *E. coli* K12 BE827/pPR29 |
| 30. | *E. coli* K12/pPR29 |
| 31. | *E. coli*/pPR29 |

We claim:

1. A recombinant DNA cloning vector comprising
   (1) a DNA segment that confers a restriction and cognate modification activity to a bacterium,
   (2) a replicon that is functional in said bacterium and,
   (3) a gene that expresses a functional polypeptide in said bacterium subject to the limitation that (1) said modification activity is expressed in said bacterium prior to said restriction activity and (2) that said gene that expresses a functional polypeptide is neither a gene that confers antibiotic resistance to said bacterium nor said DNA segment that confers restriction or cognate modification activity to the bacterium.

2. The recombinant DNA cloning vector of claim 1 wherein the gene that expresses a functional polypeptide expresses human proinsulin.

3. The recombinant DNA cloning vector of claim 1 which is plasmid pPR26.

4. The recombinatn DNA cloning vector of claim 1 which is plasmid pPR27.

5. The recombinant DNA cloning vector of claim 1 which is plasmid pPR28.

6. A transformed bacterim comprising a recombinant DNA cloning vector of claim 1.

7. The transformed bacterium of claim 6 which is *E. coli* K12 RV308/pPR27.

8. The transformed bacterium of claim 6 which is *E. coli* K12 RV308/pPR28.

9. The transformed bacterium of claim 6 which is *E. coli* K12 294/pPR27.

10. The transformed bacterium of claim 6 which is *E. coli* K12 294/pPR28.

11. The transformed bacterium of claim 6 which is *E. coli* K12 C600pPR27.

12. The transformed bacterium of claim 6 which is *E. coli* K12 C600$R_k$-$M_k$-/pPR28.

13. The transformed bacterium of claim 6 which is *E. coli* K12 BE827/pPR28.

14. The transformed bacterium of claim 6 which is selected from the group consisting of *Escherichia, Bacillus, Pseudomonas, Staphylococcus, Streptococcus, Actinomycetes* and *Streptomyces*.

15. The transformed bacterium of claim 14 which is selected from the group consisting of *E. coli* K12 RV308, *E. coli* K12 294, and *E. coli* K12 HB101.

* * * * *